United States Patent
St Amant, III

(10) Patent No.: US 10,436,678 B1
(45) Date of Patent: Oct. 8, 2019

(54) WET GAS SAMPLE SYSTEM

(71) Applicant: Mayeaux Holding LLC, Gonzales, LA (US)

(72) Inventor: Valmond Joseph St Amant, III, St Amant, LA (US)

(73) Assignee: Mayeaux Holding LLC, Gonzales, LA (US)

( * ) Notice: Subject to any disclaimer, the term of this patent is extended or adjusted under 35 U.S.C. 154(b) by 33 days.

(21) Appl. No.: 15/615,772

(22) Filed: Jun. 6, 2017

(51) Int. Cl.
*G01N 1/20* (2006.01)
*G01N 1/22* (2006.01)
*G01N 1/44* (2006.01)
*G01N 30/04* (2006.01)
(Continued)

(52) U.S. Cl.
CPC ......... *G01N 1/2035* (2013.01); *G01N 1/2205* (2013.01); *G01N 1/2247* (2013.01); *G01N 1/44* (2013.01); *G01N 30/04* (2013.01); *F24H 1/102* (2013.01); *F24H 3/02* (2013.01)

(58) Field of Classification Search
CPC .. G01N 1/2035; G01N 1/22; G01N 2001/222; G01N 2001/2223; G01N 1/2247; G01N 2001/225; G01N 2001/2285; G01N 1/2205; G01N 1/44; G01N 30/04; F24H 1/102; F24H 3/02
USPC ............... 73/863.11, 863.12, 863.81–863.85, 73/864.01, 864.02, 864.21, 864.34, 73/864.72–864.74
See application file for complete search history.

(56) References Cited

U.S. PATENT DOCUMENTS

| 3,080,760 | A |   | 3/1963 | Piersma |
| 3,133,444 | A | * | 5/1964 | Karwat ................. F17C 13/02 73/863.12 |
| 4,312,121 | A |   | 1/1982 | Tweed |

(Continued)

FOREIGN PATENT DOCUMENTS

CN 201043965 Y 4/2008

OTHER PUBLICATIONS

Research Gate, discussion regarding capillary in Gas Chromatograph, printed Dec. 12, 2017 https://www.researchgate./net/post/What_is_a_capillary_column_for_GC_and_how_does_it_work.
(Continued)

*Primary Examiner* — Robert R Raevis
(74) *Attorney, Agent, or Firm* — Joseph T Regard Ltd PLC

(57) ABSTRACT

A system for on-stream sampling of pressurized process gas such as natural gas or the like, said system optimized for use with pressurized process gas having liquid entrained therein, or otherwise referenced as "wet". In the preferred embodiment, a probe and method of sampling is contemplated to provide linear sample of fluids from a predetermined of said fluid stream. Further taught is the method of preventing compositional disassociation of a gas sample having entrained liquid utilizing a probe having a passage formed to facilitate capillary action in fluid(s) passing therethrough. The present system further contemplates a heated pressure regulator or adapter formed to thermally engage a heat trace via conducting plates and heat pipes, in order to dispense with the need for an external power source for heating. Finally, the present system further contemplates a vaporizer system or adapter therefore utilizing heat trace heating via conductor plates in lieu of a conventional internal electric-powered heat source.

10 Claims, 27 Drawing Sheets

(51) Int. Cl.
*F24H 1/10* (2006.01)
*F24H 3/02* (2006.01)

(56) References Cited

U.S. PATENT DOCUMENTS

| | | | |
|---|---|---|---|
| 4,537,071 | A | 8/1985 | Waterman |
| 4,625,570 | A | 12/1986 | Witherspoon |
| 4,688,537 | A | 8/1987 | Calkins et al. |
| 4,790,198 | A | 12/1988 | Awtry |
| 5,109,709 | A | 5/1992 | Nimberger |
| 5,154,087 | A | 10/1992 | Wenshau |
| 5,179,859 | A | 1/1993 | Van Niekerk |
| 5,237,878 | A | 8/1993 | Hackenberg |
| 5,440,941 | A | 8/1995 | Kalidindi |
| 5,501,080 | A | 3/1996 | McManus et al. |
| 5,521,130 | A | 7/1996 | Welker |
| 5,538,344 | A | 7/1996 | Dybdahl |
| 5,637,809 | A * | 6/1997 | Traina .................. G01N 1/2258 73/864.12 |
| 5,834,657 | A | 11/1998 | Clawson et al. |
| 6,357,304 | B1 | 3/2002 | Mayeaux |
| 6,605,475 | B1 * | 8/2003 | Taylor .............. G01N 27/44743 204/274 |
| 6,701,794 | B2 | 3/2004 | Mayeaux |
| 6,869,800 | B2 | 3/2005 | Torgerson |
| 6,904,816 | B2 | 6/2005 | Mayeaux |
| 7,004,041 | B2 | 2/2006 | Mayeaux |
| 7,134,318 | B2 | 11/2006 | Mayeaux |
| 7,162,933 | B2 | 1/2007 | Thompson et al. |
| 7,471,882 | B2 | 12/2008 | Peebles et al. |
| 7,958,794 | B2 | 6/2011 | Sahibza et al. |
| 8,196,480 | B1 | 6/2012 | Mayeaux |
| D674,052 | S | 1/2013 | Thompson |
| 8,522,630 | B1 | 9/2013 | Mayeaux |
| 9,200,986 | B1 | 12/2015 | Mayeaux |
| 9,257,027 | B2 | 2/2016 | Williamson |
| 9,395,280 | B2 | 7/2016 | Thompson et al. |
| 9,459,185 | B2 | 10/2016 | Thompson et al. |
| 9,535,427 | B2 | 1/2017 | Patterson et al. |
| 9,995,659 | B1 | 6/2018 | St Amant, III |
| 2010/0145634 | A1 * | 6/2010 | Pinguet ...................... G01F 1/46 702/45 |
| 2011/0036445 | A1 | 2/2011 | Hall |
| 2012/0033219 | A1 | 2/2012 | Hokamura |
| 2013/0220036 | A1 | 8/2013 | Faust |
| 2014/0041463 | A1 * | 2/2014 | Vethe ...................... E21B 41/04 73/863.51 |

OTHER PUBLICATIONS

ABB Inc, Totalflow NGC8206 Chromatograph User's Manual, (C) 2009, Ver 2101510-002-rev.AE, US, See pp. 1-17, 2-25 & 2-58 thru 2-64.
ACME Cryogenics, ACME Model CV Cryogenic Valve Brochure, US p. 2, 2013.
Federal Register, vol. 81, No. 222 BLM 43 CFR Parts 3175.111-112 "Onshore Oil and Gas Operations; Federal and Indian Oil and Gas . . . " Nov. 17, 2016, pp. 81578-81580 US.
ACME Cryogenics, Vacuum Insulated Pipe brochure, US, 2014.
ABB Inc, Portable NGC8206 Natural Gas Chromatograph DS_2101179, Copyright 2017, US.
Cryofab CFCL Series Vacuum Insulated Flexible Hose leaflet, US, 2015.
A+ Corp LLC, Genie tm High Velocity Probe Product Sheet, PPS-SGP-HV-120803, Copyright 2003 US.
Intertec, SL Blocktherm Self-Limiting Block Heater Product Sheet, HD-662ca, 2013.
Valtronics Inc, Mustang Sampling Sample Conditioning System MSCS P53, MSB-P53 vol. 1.2 (C) 2009.
Valtronics, Inc Mustang Sampling Pony Heated Probe Encl PONY, MSB-PONYCS vol. 2.1 (C) 2009.
Welker, Sample Conditioning Heated System Manual, Model SCHS, Manual IOM-132, Rev C, Apr. 20, 2016 , p. 6.
Intertec, Diabox 87 Product Sheet, KD222-12en Diabox 87, 2017.
Mustang Sampling LLC, MSCS Product Brochure, MSB-MSCS vol. 1.5, (C) 2009-2017.
Mustang Sampling LLC, Solar Powered Sample Conditioning System SPSCS Product Brochure MSB-PonySOL vol. 2.1 (C) 2014-2017.
Mustang Sampling LLC Sample Conditioning System P53 Product Brochure MSBC-P53-CE vol. 2.2 (C) 2009-2017.
Mustang Sampling LLC PONY Heated Probe Enclosure Product Brochure MSBC-C-PONYCS vol. 4.4 (C) 2009-2017.
A+ Corp LLC, GENIE Heated Regulator GHR Product Sheet, SCC-GHR-PS_0906 (C) 2006.
A+ Corp, LLC, Genie, GHR Heated Regulator Product Sheet, SCC-GHR0PS_1116 (C) 2012.
A+ Corp, LLC, GENIE GPHV General Purpose Probe Product Sheet, SCC-GPHV-PS_0116, (C) 2012.
A+ Corp, LLC, GENIE Vaporizer Product Sheet, SCC-GV-PS_0106, (C) 2006.
A+ Corp , Genie 760 Direct Drive Probe Product Sheet, SCC-7600PS_0116, (C) 2012.
United States Patent Office, "Non-Final Rejection" in U.S. Appl. No. 14/214,225 (now U.S. Pat. No. 9,995,659), St Amant, III inventor, dated Jun. 5, 2017, 11 pages.
United States Patent Office, "Final Rejection" in U.S. Appl. No. 14/214,225 (now U.S. Pat. No. 9,995,659), St Amant, III inventor, dated Nov. 10, 2016, 13 pages.
Matheson Gas, "The BTU Accuracy Connection to Profitability . . . ", 2 page brochure, 2010.
US Dept of Interior, BOL Operator Letter (redacted) Mailed Jan. 19, 2017, US.
Thermon Manuf Co, Brochure PAF00270714 "installing Non-Heated Wires within a Tube Bundle", Thermon Manuf Co, undated, US, 2014.
Mustang Sampling LLC, Mustang Intelligent Vaporizer Sampling System Model 2, Product Sheet, Mustang Sampling LLC, Ravenswood, WV, (C) 2009-2016, US.
Welker Inc, SCHS Sample Conditioning Heated System, Product Sheet, Welker, Inc, Sugar Land, TX (C) 2016, US.
McMaster-Carr Supply Co, Web Catalog at https://www.mcmaster.com/#catalog/123/1/=1ap8126, Stainless Steel Tubing, p. 143, downloaded Dec. 26, 2017, US.
Research Gate, discussion regarding capillary in Gas Chromatograph, printed Dec. 15, 2017 https://www.researchgate./net/post/What_is_a_capillary_column_for_GC__and_how_does_it_work.
McMaster-Carr Supply Co, Web Catalog, https://www.mcmaster.com/#catalog/123/153, Extreme-Pressure Stainless Steel Tubing, 2016, p. 153, 2016, US.

* cited by examiner

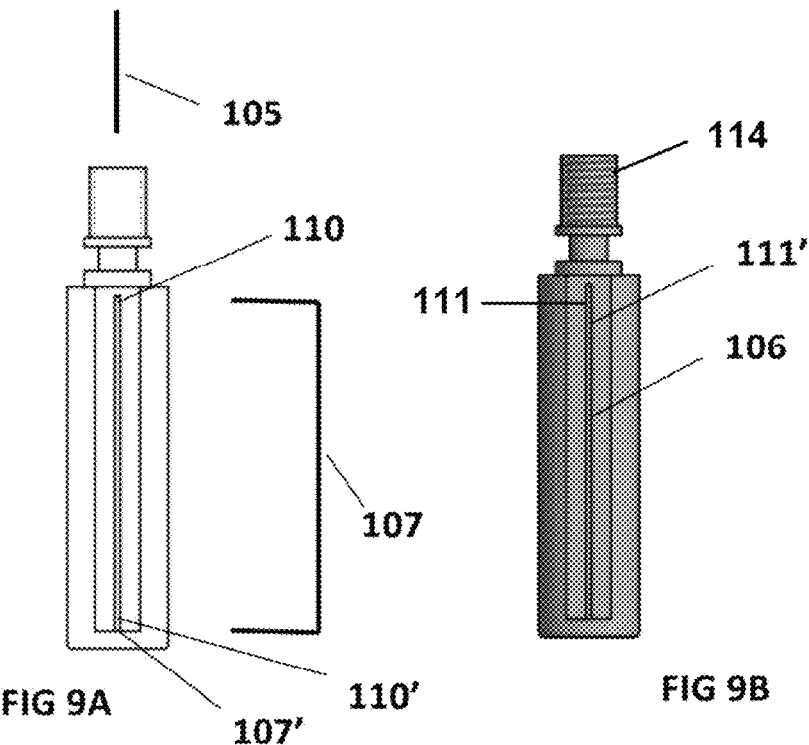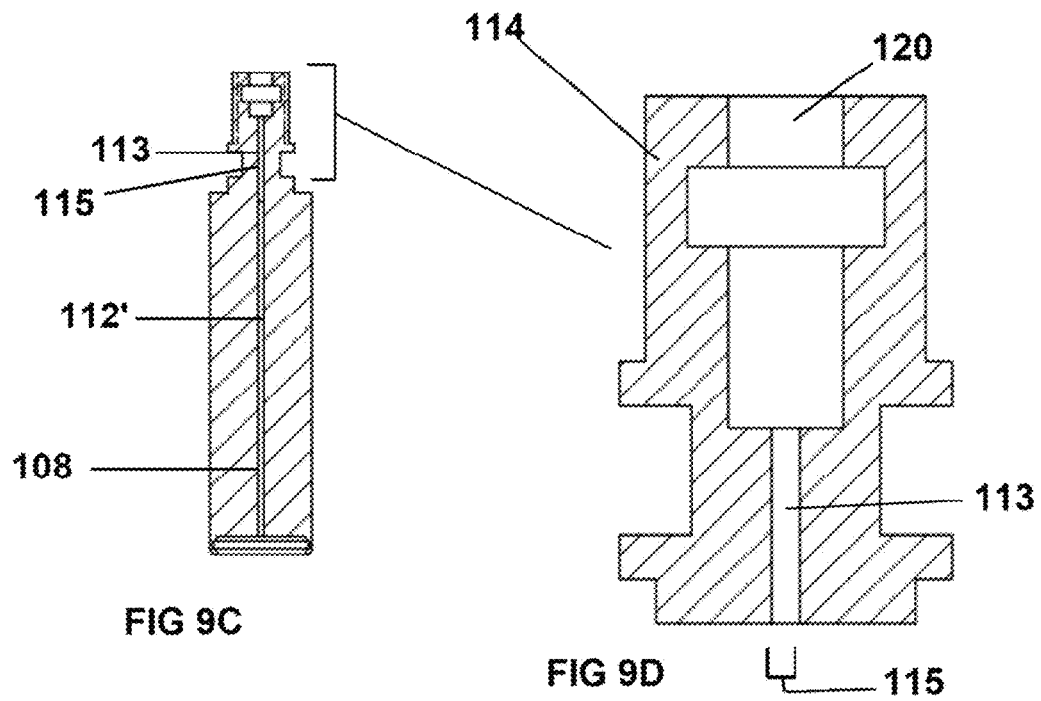
FIG 9A FIG 9B FIG 9C FIG 9D

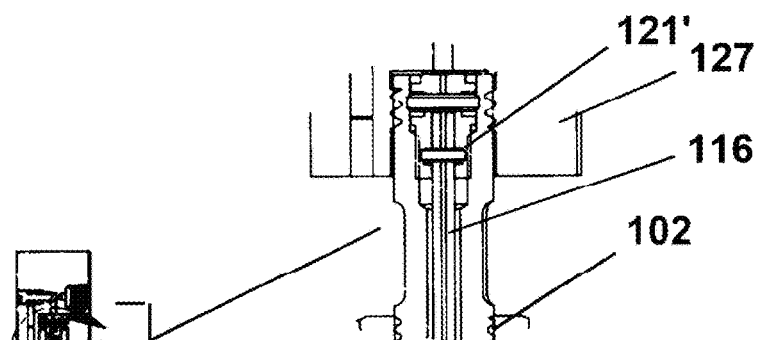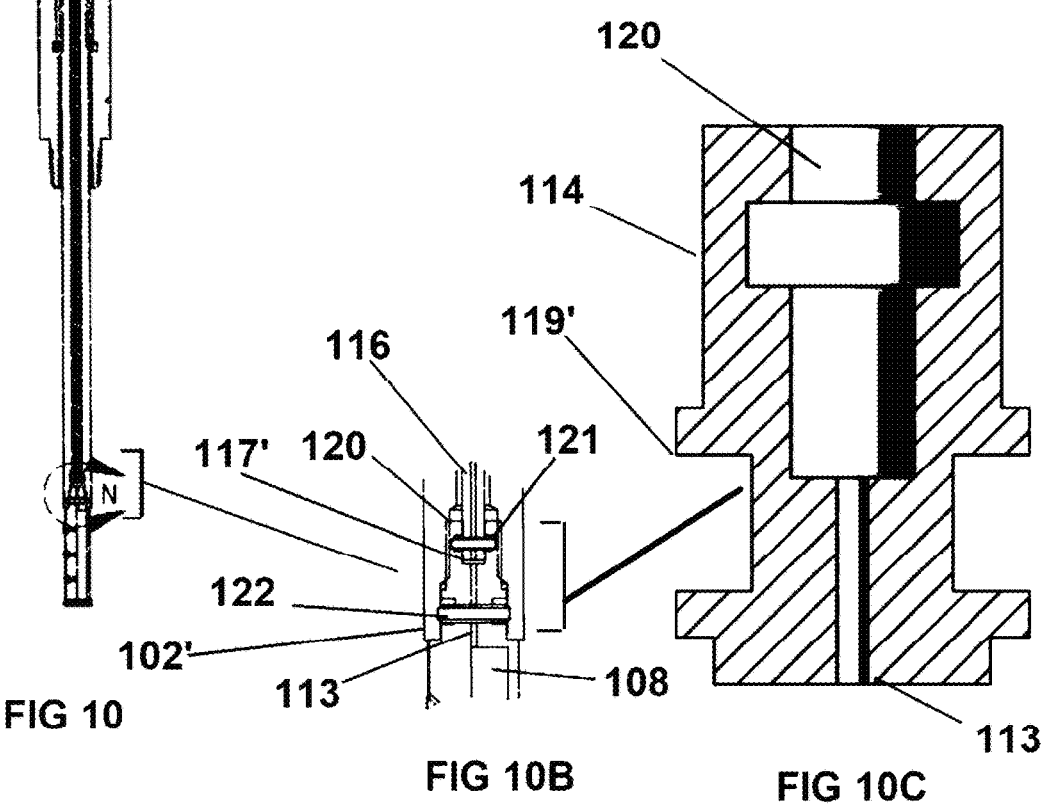
FIG 10A
FIG 10
FIG 10B
FIG 10C

FIG 21A  FIG 21B  FIG 21C 14
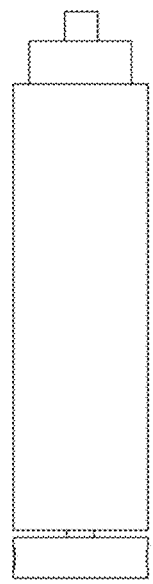
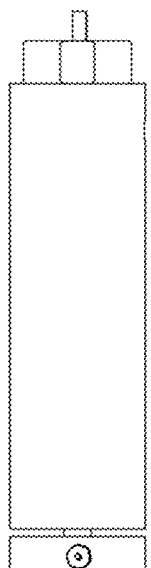
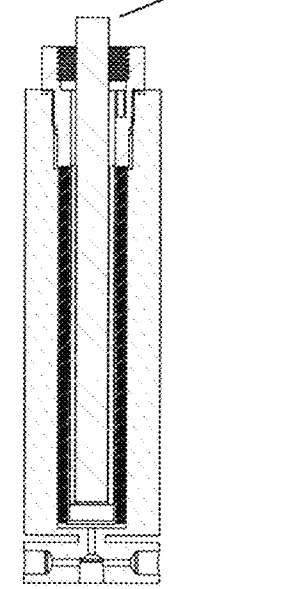
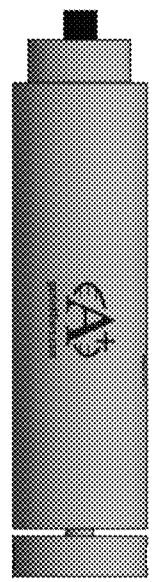
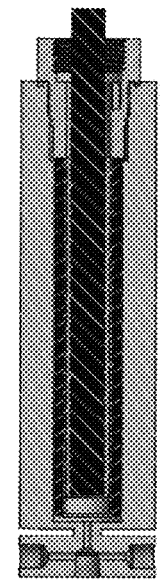
FIG 21D  FIG 21E  FIG 21F

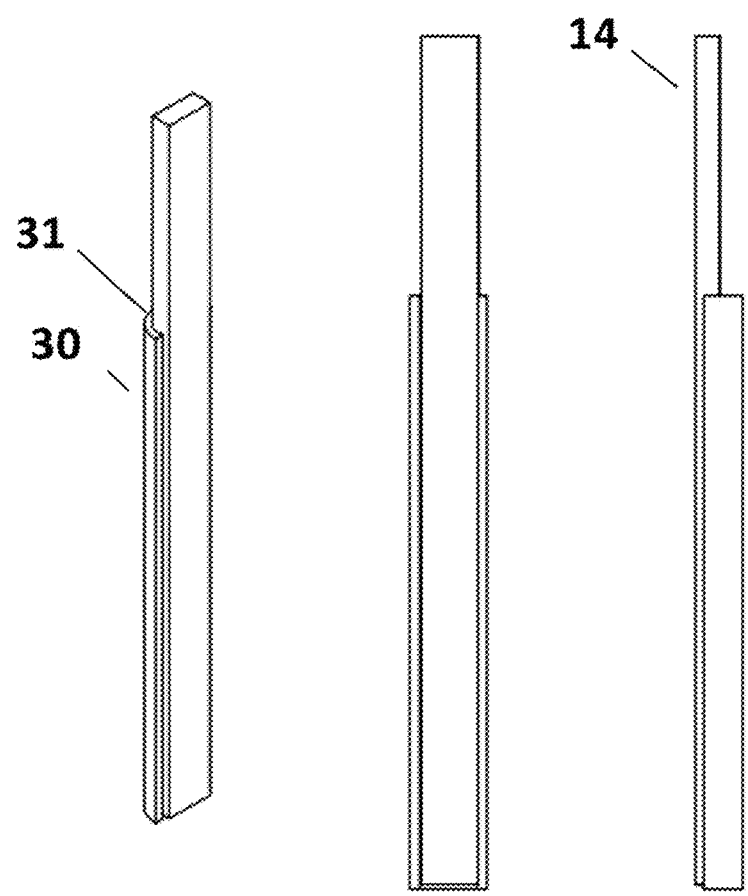

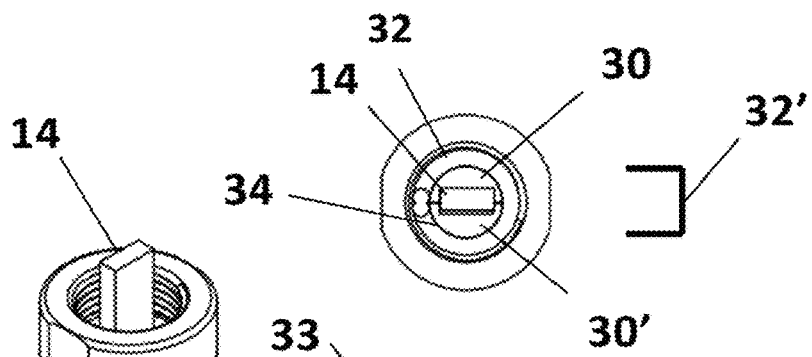
FIG 24C
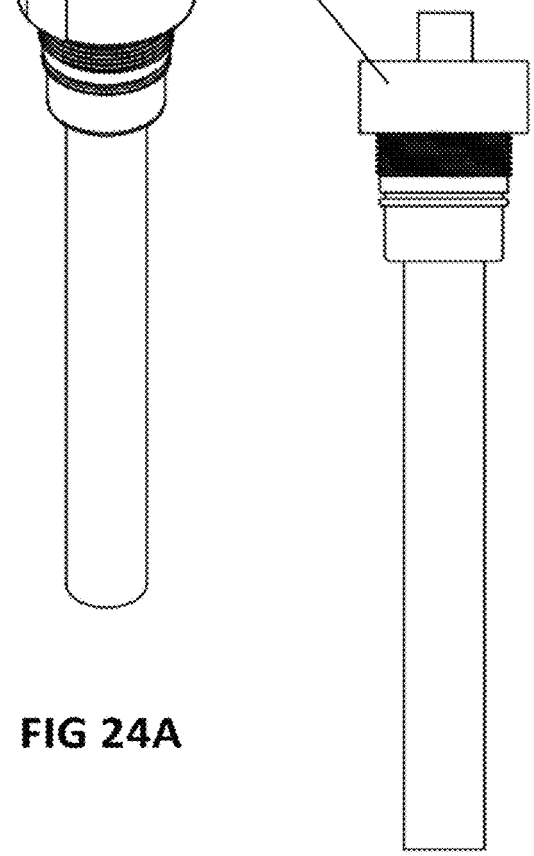
FIG 24A
FIG 24B

WET GAS SAMPLE SYSTEM

FIELD OF THE INVENTION

The present invention relates to sampling of pressurized process fluids, and more particularly a system for on-stream and/or spot sampling of pressurized process gas having liquid entrained therein, otherwise known and referenced as multiphase or "wet" such as natural gas or the like. The invention contemplates a unique probe formed to take a linear sample of fluids at a predetermined area of said fluid stream, including the center-third, in compliance with recent Bureau of Land Management (BLM) requirements. The present invention also contemplates a unique system for facilitating thermal equilibrium with the fluid stream, utilizing a heat trace and interface formed to evenly distribute heat transfer and engage a vaporizer, pressure regulator or other modular conditioning component via thermal conductor plates. The present invention provides a sampling system compliant with newly-revised BLM orders, and is particularly suitable for use in BLM regulated areas with limited electrical power availability.

BACKGROUND OF THE INVENTION

Natural Gas is comprised of a mixture of gases (See API 14.1 Section 6.3 and naturalgas.org). Natural gas is bought and sold based on its heating value (BTU), which is derived from a compositional analysis of the natural gas. It is the BTU content that determines the monetary value of a given volume of natural gas. This BTU value is generally expressed in decatherms (one million BTU).

To determine the total heat value of a given volume of gas, a sample of the gas is analyzed, and from the compositional data, its heat value per unit volume is calculated. This value is generally expressed in BTU/cu ft. The typical range of transmission quality gas ranges between 1000 and 1100 BTU/cu ft. Production gas, storage facility gas, NGL, and new found Shale Gas can have much higher heating values up to or even exceeding 1500 BTU/cu ft.

There has been a long-standing controversy between gas producers and gas transporters regarding entrained liquid typically present in most high BTU/cu ft. gas (rich or "wet" gas). Transporter tariffs require essentially liquid-free gas. Liquid in the gas being transported causes operational and safety problems. The practice is to separate the liquid before entering a transport (pipe) line.

The API 14.1 standards (Manual of Petroleum Measurement Standards, 2006) scope does not include supercritical fluid (dense phase) or "wet gas" "(a term referenced by the Natural Gas industry as a gas that is at or below its hydrocarbon dew point temperature and/or contains entrained liquid), nor does the GPA 2166 standard (Obtaining Natural Gas Samples for Analysis by Gas Chromatography, 2005). In summary, there is no known standard which defines how to obtain a "representative sample" of a natural gas supply having entrained liquid in any form.

Therefore, to fully comply with the current industry standards, membrane-tipped probes such as the A+ Corporation Genie Probe (see U.S. Pat. Nos. 6,357,304, 6,701,794, 6,904,816, 7,004,041, and 7,134,318) have been used for many years to shed entrained liquids inside pressurized pipelines. Electrically powered heaters may be provided, which are powered by a separate power line included in the tube bundle. This power line is separate from the heat trace.

Companies such as Mustang Sampling, LLC have bolted enclosures to the A+ Corporation membrane-tipped probes, and are believed to utilize third party, electrically-powered heater blocks and A+ Corporation cartridge-type heated regulators for the enclosure, as well as third party electrical heat trace products. See for example U.S. Pat. No. 7,162,933. See also U.S. Pat. No. 9,459,185 relating to a solar powered sample analyzing system. See also ABB NGC8206 User Manual, Copyright 2009, Pages 1-17 and 2-58 through 2-64, available for download at their website.

Other housing or enclosure providers include, for example, vendors such as Intertec Hess GmbH's instrumentation component offerings on the internet at www.Intertec.info—Intertec Hess is not only a provider of enclosures but is also a provider of the electrically-powered heater blocks. Splicing kits suitable for such an application may be found at Protherm Industries Inc website, which offers, for example, a FE Series Splice Kit which could be used in this application; splice kits also available from other third party providers such as Pentair at their website.

Mustang Sampling, LLC Brochures MSB-PONY and MSB P53, available at their website, can include products incorporating A+ Corporation Genie membrane tipped probes, and utilize third party, electrically-powered heater blocks and A+ Corporation cartridge-type heated regulators and third party heat trace, as described above. Mustang Sampling brochure MSB P53 illustrates a product which can include A+ Corporation GENIE brand membrane separators (U.S. Pat. No. 7,555,964, a CIP of U.S. Pat. No. 7,097,693 (listing the present Inventor as second Inventor)) in an enclosure, which is ideally mounted in the vicinity of the analyzer, which may include additional electrically-powered heater blocks and electrically powered heated regulators (See Mayeaux U.S. Pat. No. 6,357,304, Thompson U.S. Pat. No. 7,162,933, and Thompson US 2012/0325694 A1).

Other companies such as Welker Engineering use non-membrane probes (fixed probes) and bring the liquids outside the pipeline to reject the liquids inside enclosures containing an electrically powered heated regulator and then returning the liquid back to the pipeline, while hanging a hinged enclosure onto the probe (see Welker SCHS manual, page 6, at their website, and U.S. Pat. No. 7,471,882). The purpose of these sample systems is to reject entrained liquids and maintain the sample system temperature above the sample dew point to prevent further condensation.

The above and other known prior art rely upon power being readily available for electrical cartridge heater devices and electrical heater blocks to provide heat for the sample systems, or vacuum jacketed tubing that has been used commercially for liquified natural gas sample systems for decades. Vacuum jacketed tubing providers include companies like Acme Cryogenics and Cryofab. Also see Thompson U.S. Pat. No. 9,395,280 B2.

Recently the Bureau of Land Management (BLM) has revised 43 CFR 3175 (Order 5) The Onshore Oil and Gas Operations, Federal and Indian Oil and Gas Leases, Measurement of Gas effective Jan. 17, 2017, as indicated in the Federal Register, Vol 81, No 222, Sections 3175.111 and 3175.112, pages 81578-81580, issued 17 Nov. 2016.

Sections 3175.111 and 3175.112 now mandate a sampling protocol that is outside of the scope of API 14.1 and GPA 2166, by mandating sampling of two-phase samples (gas with entrained liquids) without rejecting the liquids, to provide a sample to the analyzer. The new BLM order tries to reference parts of API 14.1 and GPA 2166, but it is clearly outside the scope of both of those industry standards. In addition, the new BLM order forbids the use of membranes or any other type of filter and means of liquid rejection in the probes used to take the sample. Therefore, contaminants like glycols and amines will no longer be rejected, filtered, or removed from the sample that is taken from the pipeline. The new order requires liquids and gases to be removed from the center third of the pipeline and heated sample lines to vaporize any liquids removed before they reach the analyzer.

Many of these sample points are in small diameter pipelines with limited electrical power available, or only low wattage close proximity solar power available. Solar power has been traditionally used in natural gas sampling for decades. See U.S. Pat. No. 5,501,080A, McManus et al, claiming a 1994 Priority date as one example as well as Thompson U.S. Pat. No. 9,459,185 and vendors such as ABB (See the ABB NGC8206 user manual pages 1-17 and 2-58 through 2-64, copyright 2009, available at the company website).

Most of the BLM sample points will only have solar power available for the short distance of self-limited heat trace tubing, but will be required to heat and vaporize the samples. Many of these BLM regulated locations will utilize portable low power gas analyzers that are powered from the technician's vehicle instead of on-site stationary conventionally powered gas analyzers such as gas chromatographs or other types of gas analyzers.

GENERAL SUMMARY DISCUSSION OF THE INVENTION

The present invention is configured to provide a single-phase gas sample to the analyzer without rejecting the liquids, in limited or low power areas, providing a unique sample system which is compliant with new BLM order 5, and without the problems and shortcomings associated with the prior art sample systems referenced above.

The present invention does not require the use of membrane filters or any other filter or method that would reject liquids. The present system contemplates a unique probe formed to take a linear sample of fluids at the medial area of said fluid stream. The unique design and method of operation makes it particularly suitable for BLM order 5, providing compliant sample probes and methodologies. The present invention is also uniquely designed to heat and vaporize the sample without the need for separate electrical power.

Unlike the above discussed, prior art sampling systems, the present invention teaches a new and innovative "integral slice" sampling process, wherein a very thin slice of the total volume of the source fluid flowing through a conduit or pipeline is captured by a streamlined container arrangement suspended in said source fluid, in a similar manner to an integral in calculus—a limiting procedure which approximates the area of a curvilinear region by breaking the region into thin vertical slices—with nominal flow disturbance, and in which trapped fluid is subsequently withdrawn and isolated in a location outside of the source fluid flowing stream.

Further, unlike dynamic isokinetic techniques, the system of the present invention insures that the representative sample taken either in spot, batch or continuous fashion is not allowed to disassociate due to the very small internal cavity of the slot and outflow passage following the slot. Empirical testing verifies that, if the diameter of the passage is sufficiently small, then the combination of surface tension (which is caused by cohesion within the liquid and adhesive forces between the liquid and container wall) and the higher velocity sweep will act to propel the liquid as well as the gas, preventing disassociation. The pipeline area is very large compared to the probe's very small interior and because of this vast difference; fluid in the probe will always be of a higher velocity than the pipeline fluid.

The high gas velocity (higher than the source velocity of the pipeline) of the very small internal cavity would then sweep the all of the liquid particles at the same velocity as the gas particles being transported from the source to the probe. Therefore, it would remain "associated" with the gas from which it condensed. Small particles such as that which comprise smoke are known to behave somewhat like large molecules. High velocity gas in the small internal diameter bore of the probe will prevent any significant layer of liquid from accumulating on the surfaces. Even if an ultra-thin layer were to coat the probe's interior, the total area is so small that the impact would be negligible.

The present invention provides a far superior sampling solution for wet gas streams, including high HC dew point gases, which traditionally have been difficult to sample dynamically due to phase changes and resulting composition changes which can be triggered by flow, pressure, and/or temperature.

The present invention is a unique sample system designed to solve the problems of prior art sample systems while complying with the new BLM order 5.

The inlet of the present invention features a capillary passage following the linear-slot probe. The capillary passage may be in the form of a passage formed in the probe or capillary tubing inserted therein. In either case, the passage is formed to facilitate capillary action or motion, and higher velocity in "wet gas" flowing therethrough, to prevent the two-phase sample from disassociating as it is transported to the unique, passively-heated pressure reducing regulator.

As discussed above, prior art systems require a separate electrical power line in the tube bundle or the electrical power from the heat trace to electrically power additional electrically powered devices such as heater blocks or electrically powered heated regulators. However, the additional electrical power required adds additional electrical load that may surpass the limited available power and may use wattage that was needed for the heat trace in limited electrical supply areas in BLM locations. Many of these BLM locations utilize a portable low power analyzer that is powered from the technician's vehicle.

Rather than being heated by electricity directly, the conditioning devices of the present invention are passively heated by a unique thermal conductor plate interface. The thermal plates are designed to thermally engage the heat trace, preferably at its termination end, the heat trace often already in use at the sample location (and powered by solar panels already in place, for example), so that no additional electrical device or heater is required.

A first exemplary modular conditioning component is in the form of a pressure regulator, which has emanating therefrom heat pipes formed to engage the thermal conductor plate interface to conduct heat from the heat trace engaging the thermal conductor plates to the area of the pressure regulator base housing the valve stem where the pressure drop takes place, to offset the joules-thompson (JT) cooling effect, which base is formed to receive the heat pipes (in lieu of the standard electrically heated base).

This unique pressure reducing regulator design is not believed to require electrical agency approval as it does not use any electrical power, nor does it require fuel so it has no source or need for ignition. Accordingly, this system can be placed in any electrically classified area that the heat trace is approved for use.

An exemplary pressure reducing regulator which can be utilized with the present invention, which some modification (as discussed herein) is the GENIE brand heated regulator GHR, as provided by A+ Corporation, LLC but without the electrical heated base (utilizing the unique base formed to engage the thermal conductor plate interface, discussed above, the thermal conductor plates preferably formed of Aluminum for this application). The Model GHR utilizes a pre-heated gas path as well as a post-heated gas path.

If the GHR system of the present invention lacks sufficient heat to vaporize the liquid passing therethrough on its own, a Vaporizer formed to engage specially configured thermal conductor plates thermally interfacing the heat trace (preferably of brass for this application) can be provided. An exemplary Vaporizer which can be utilized with the present system is the Genie GV vaporizer as provided by A+ Corporation LLC, but with a modification wherein the GV electrically heated parts are replaced with a unique brass block forming the thermal conductor plates that envelope the heat trace, and evenly distribute the heat, as discussed herein.

The low wattage used by the heat trace allows the use of conventional industry standard solar panels that have been used commercially for sample systems since the 1990s. For example, see U.S. Pat. No. 5,501,080. To minimize the loss of heat due to the environment, the assembly is inside a unique housing/enclosure.

With the above discussed innovations, the present invention provides a unique modular conditioner/sampling system which, unlike the prior art, is not designed to specifically reject entrained liquids. Instead, the present system is designed to be fully compliant with BLM order 5.

To prevent sample distortion after the probe, the capillary passage with associated higher velocity following the linear-slot sampling probe of the present invention does not allow the two-phased sample to disassociate before it is vaporized by the uniquely passive heated pressure reducing regulator. These components are located inside a unique housing/enclosure that facilitates 100% access to all components. It accomplishes this objective without any hinges or diagonal cuts. The system is designed so that the enclosure is independent of the probe and the components. The enclosure can be easily and completely removed without disturbing the probe or any other components of the system, while protecting the components and decreasing heat loss.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 9A is a close-up, frontal view of the invention of FIG. 7A.

FIG. 9B is a greyscale view of the invention of FIG. 9A.

FIG. 9C is a side, partially cut-away, partially cross-sectional view of the invention of FIG. 9A.

FIG. 9D is a side, partially cut-away, partially cross sectional, detailed view of the threaded end of probe 114 and outflow passage 113 of FIG. 9C.

FIG. 10 illustrates a side, partially cut-away, partially cross-sectional view of the probe with slotted probe tip of the present invention having the capillary line through the length of the probe via probe passage, passing through the probe first end, rack, and the second end to probe tip.

FIG. 10A is a side, partially cut-away, detailed view of the first end of the capillary tube engaging a flow component for flow out of the probe, sealed via O-Ring.

FIG. 10B is a side, partially cut-away, detailed view of the second end of the capillary tube engaging a receiver formed within the threaded area of the slotted probe tip of the present invention, via sealed O-rings.

FIG. 10 C is a cross-sectional, close-up, side view of the receiver formed to receive the capillary tube in the threaded area of the slotted probe tip.

FIG. 11 A is a side view of an improvement to the device of FIG. 11, utilizing heat pipes (not shown) in lieu of electrical power, the device mounted on bracket 11.

FIG. 21A is a first side view of the invention of an improvement in heating modular conditioning components, in the present figure, an embodiment of the invention for heating an off-the-shelf vaporizer or the like, the illustrated invention formed to heat via heat trace, instead of the electrical heater as shown in FIG. 20.

FIG. 21B is a second side view of the vaporizer of FIG. 21A.

FIG. 21C is a cross-sectional view of the vaporizer of FIG. 21A.

FIG. 21D is a greyscale rendition of FIG. 21A.

FIG. 21E is a greyscale rendition of FIG. 21B.

FIG. 21F is a greyscale rendition of FIG. 21C.

FIG. 22A is a perspective, partial, close-up, partial view of the invention of FIG. 21C, illustrating a first heat conducting cover having a slot formed along its length to receive a heat trace.

FIG. 22B is a side view of the heat conducting cover with heat trace of FIG. 22A.

FIG. 22C is an edge view of the heat conducting cover of FIG. 22A engaging heat trace 14.

FIG. 24A is a perspective view of the invention of FIG. 23A, FIG. 24B is a side view of the invention of FIG. 24A.

FIG. 24C is an end view of the invention of FIG. 24A, illustrating the location of the heat trace, and first 30 and second 30' heat conducting covers 30, 30", illustrating the opposing first and second heat conducting covers enveloping the heat trace 14, engaging and situated inside the cartridge housing formed to engage the vaporizer which had been previously used for the electrical heater cartridge, but now used to house the heat trace engaging cartridge formed by first and second heat conducting covers 30, 30'.

DETAILED DISCUSSION OF THE INVENTION

Preferably, the sample conditioning system of the present invention (FIGS. 1-25b) is mounted at the source of the sample, in this case a pipeline having pressurized process gas.

A substrate coupling 4 is provided to provide a base for connection of the process flow to the modular sample system 5. The substrate coupling is mounted to the process isolation valve 3. The coupling 4 connects the process source 1 to the modular sample conditioning system of the present invention. Enclosure 16 is engaged to and supported by the substrate coupling 4, and is provided to house and protect the modular components (as further discussed herein). FIG. 3 is a cutaway view of FIGS. 1-2.

Linear Sample Probe and Method of Sampling

Figure 1:
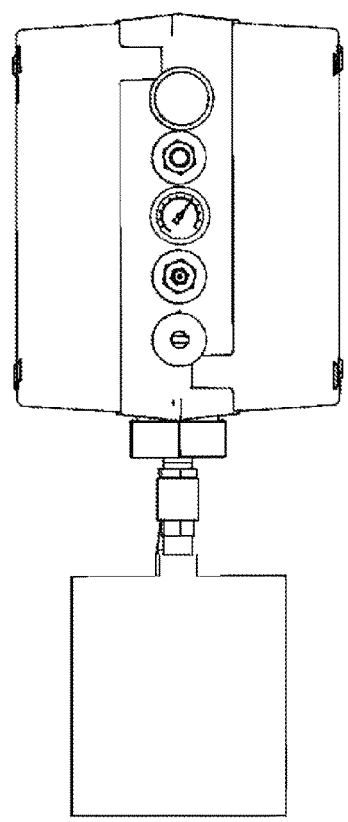
FIG. 1 is a frontal view of a sample modular sample conditioning system comprising modular sampling and/or conditioning components mounted to a substrate bracket, enclosed via a housing/enclosure.
Figure 2:
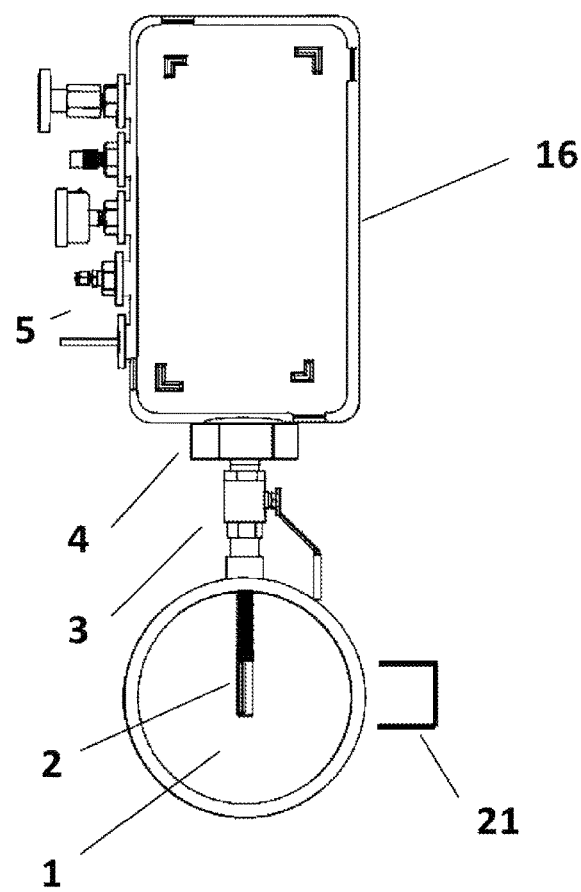
FIG. 2 is an side view of the invention of FIG. 1, further showing an end view of the source of gas with entrained liquids, a linear sampling probe of the present invention situated therein, providing a passage to the modular sampling/conditioning components via substrate coupling 4.
Figure 3:
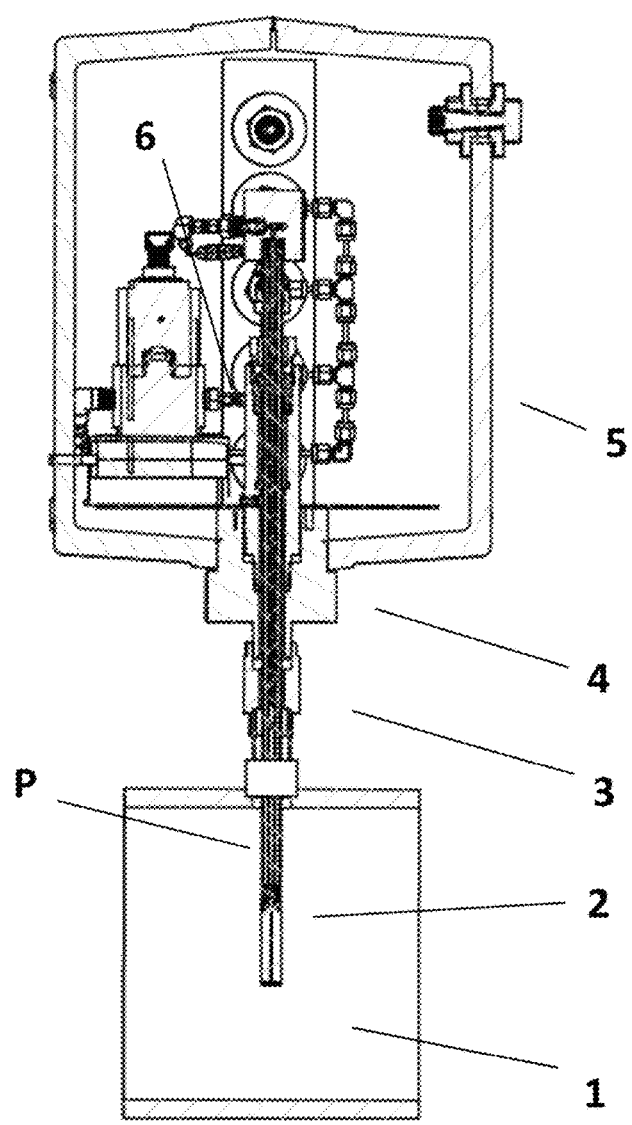
FIG. 3 is a rear, partially-cut-away view of the invention of FIGS. 1-2, illustrating the linear sampling probe of the present invention, the substrate coupling to prevent the disassociated collection of gas having entrained liquids therein.
Figure 4:
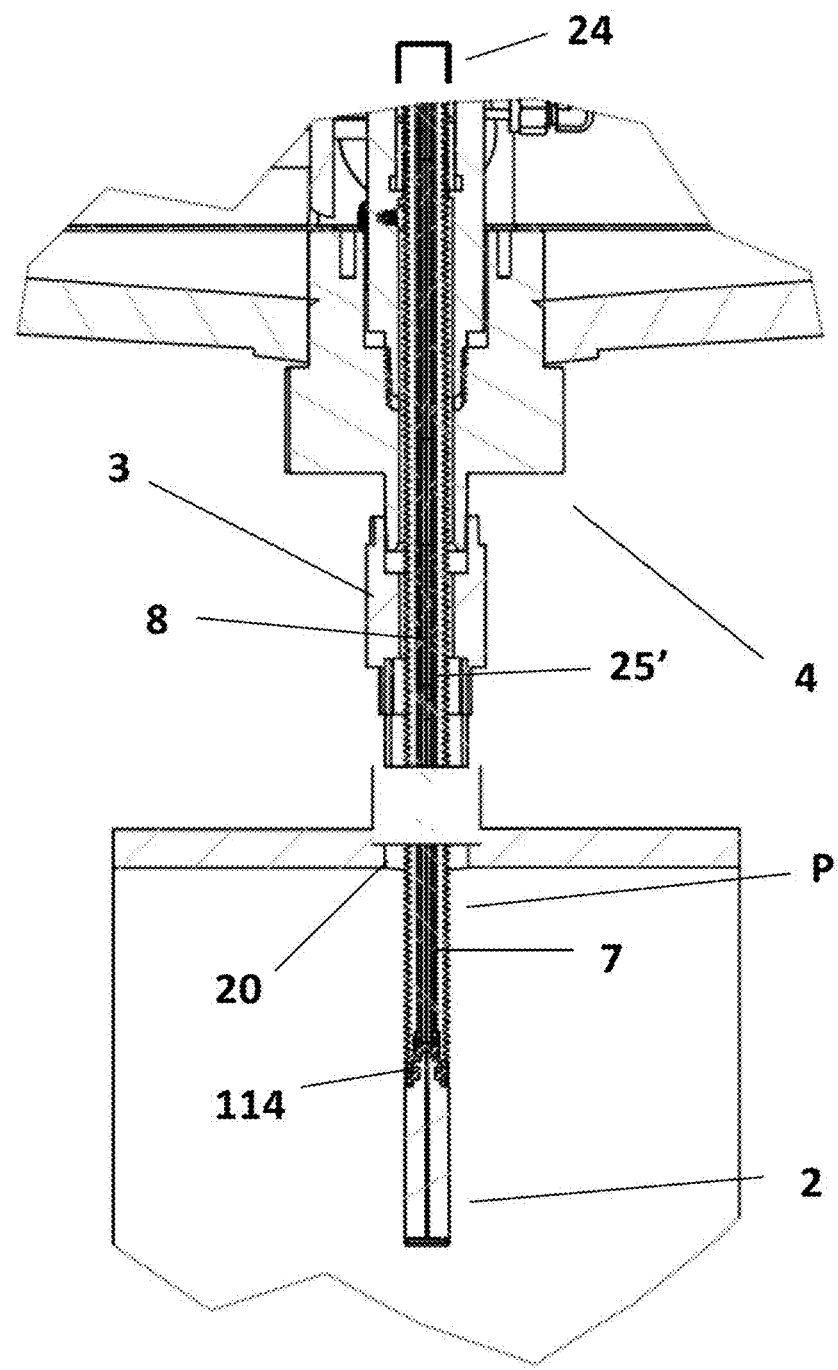
FIG. 4 is partial, close-up view of the probe and substrate FIG. 3.
Figure 5:
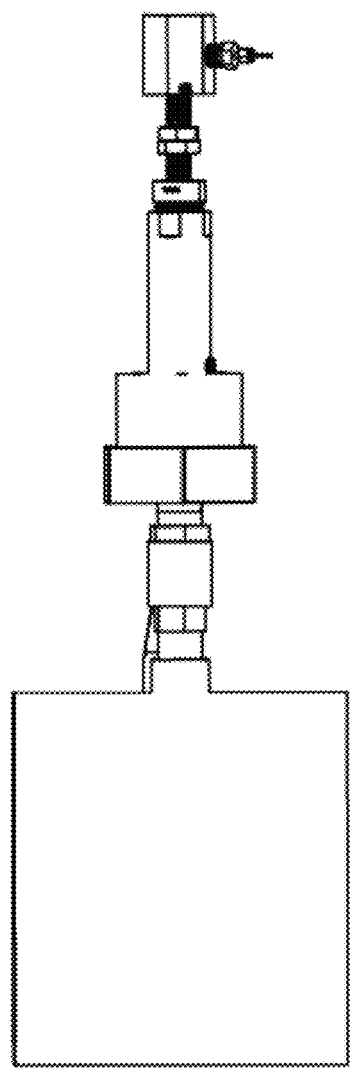
FIG. 5 is a side view of a pipeline containing a process gas flow having a linear sampling probe mounted thereto to sample the contents therein.
Figure 6A:
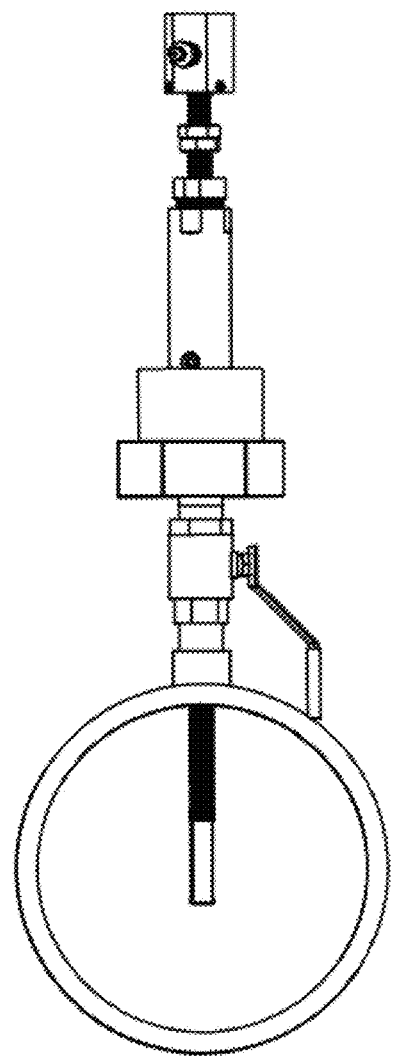
FIG. 6A is an end view of FIG. 5 showing the linear sampling probe with probe tip positioned at the center-third, medial area of the pipeline, so as to provide a center-third, medial sampling of same.
Figure 6B:
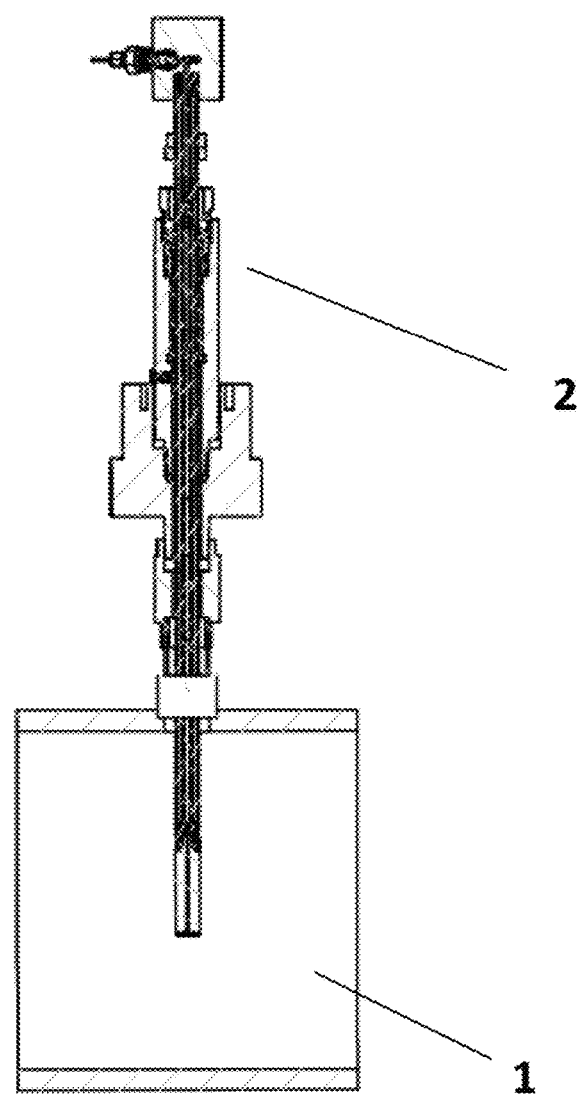
FIG. 6B is a side, sectional, cut-away view of FIG. 5 showing the insertion mechanism supporting the probe tip.
Figures 7A, 7B:
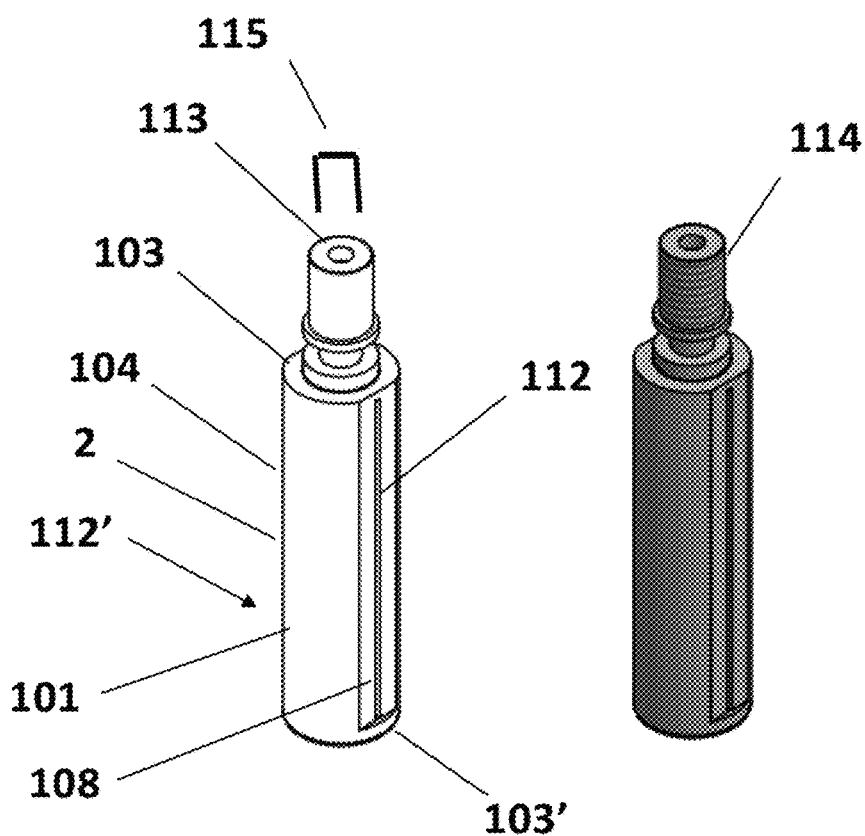
FIG. 7A is an isometric, front view of the probe of FIGS. 5-6B, illustrating the linear slot formed along the length of the body and threaded connection end with capillary passage.
FIG. 7B is a greyscale view of the probe of FIG. 7A.
Figures 8A, 8B, 8C:
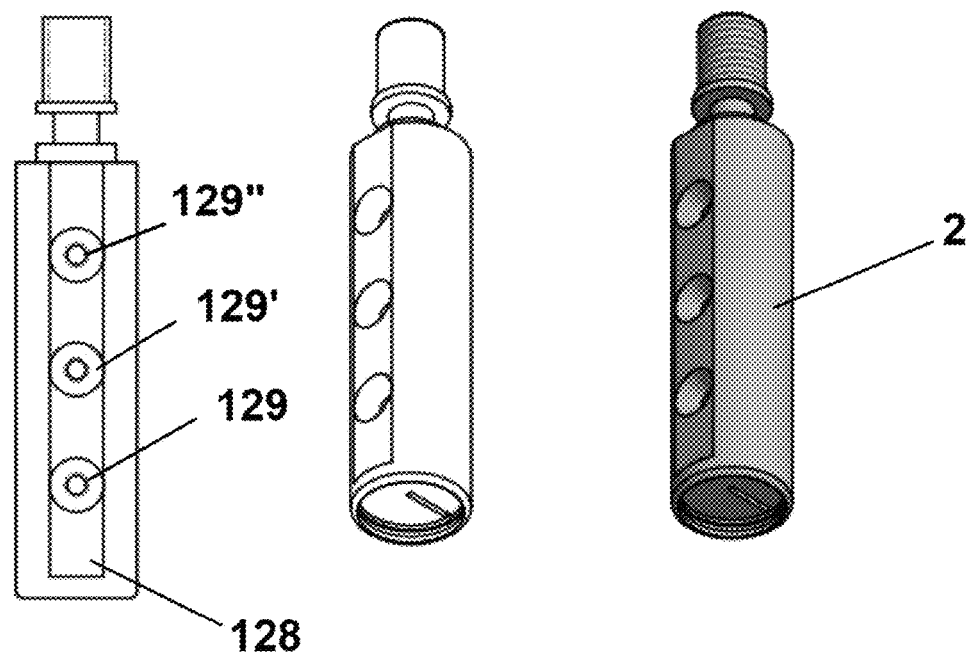
FIG. 8A is a rear view of an embodiment of the probe of FIG. 7A, illustrating a series of tapped holes or screws situated in spaced relationship along the length of the rear of the probe, for holding an optional screen filter sized to prevent solid particulates from entering the slot.
FIG. 8B is a perspective view of the invention of FIG. 8A, illustrating the position of the forward sampling slot in relation to the tapped holes.
FIG. 8C is a greyscale view of the invention of FIG. 8B.
Figure 8D:
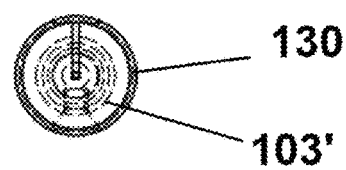
FIG. 8D is a bottom, partially cutaway view of the invention of FIG. 8A.
Figures 10D, 10E:
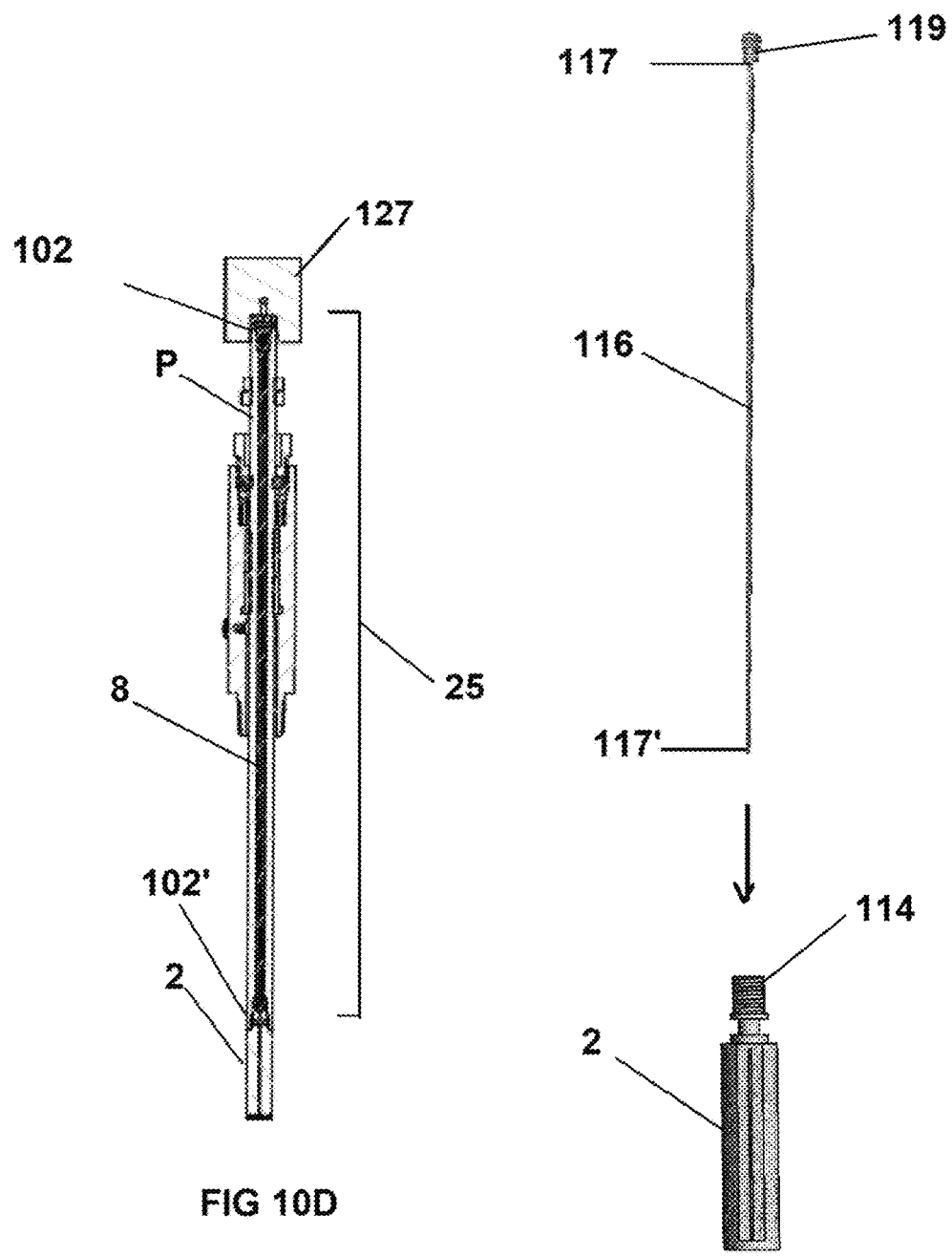
FIG. 10D is a side frontal, partially cut-away, partially cross-sectional view of the probe with slotted probe tip of FIG. 10.
FIG. 10E is a side frontal view of the probe tip of the present invention, illustrating the capillary tube aligned for insertion therein (the capillary tube will be positioned to pass through the probe to the probe tip as will be discussed herein).

FIGS. 1-2 shows pressurized source of gas (a/k/a process source) with entrained liquids 1 with the linear, slotted sampling probe tip 2 positioned in the fluid stream so that the collection slot faces the fluid flow, the probe tip shown position in the center-third area to sample the center-third 21, medial area of the flow stream, although the probe length and associated collection area can be modified as required. As shown, a probe isolation valve 3 is provided to selectively open and close the flow from the probe to the modular sample conditioning system 5, as required. As shown, the probe P, has a length 25 and first 102 and second ends 102', as will be further discussed herein. For insertion, a rack 25' may be provided along the probe P length as shown in FIG. 4.

Referring to FIGS. 7A-10E, formed through the outer wall 104 of body 101 of linear sampling probe tip 2 is an elongated, continuous or uninterrupted opening 106 having a length 107 aligned with the longitudinal axis 105 of the body 101, the opening 106 having a relatively narrow width 107', and ends 110, 110' to form a slot 108 penetrating the outer wall or surface of the body, the slot forming first 111 and second 111' side walls within the body forming an outer edge 112 and an inner edge 112' corresponding to its depth and providing a passage to outflow passage 113 having a small inside diameter as shown.

In the preferred embodiment of the invention shown in the figures, the slot 108 preferably has a relatively uniform width 107' preferably corresponding to, or less than, that of opening 106, while providing passage about to the longitudinal 105 body 101 at the innermost edge 112' of the slot, about halfway through body 101. The slot as shown runs along longitudinal axis 105, although the length and position of the slot can vary depending upon the application.

As shown, the slot 108 in the exemplary, preferred embodiment of the probe tip of the present invention runs from just below the first 103 end of body 101 to about the second end 103' of body 101, with the inner edge 112' of the slot 108 engaging outflow passage 113 having a small inside diameter 115, as shown, which is formed to engage, as required, (FIG. 3) insertion probe P to provide a channel of flow of fluid therefrom, the outflow passage 113 in the present embodiment preferably having an inner diameter 115 preferably equal to or less than the width 107' of slot.

The present system is formed to collect via the slot in the slotted probe tip a "linear sample" spanning a pre-determined area for sampling of the pipe, in the preferred embodiment of the present invention, the center-third area of the flow as is illustrated in FIGS. 1-6B and 19B, or (in other versions) alternatively other zones or even the full span of the pipe from side-wall to side-wall, providing a representative sample of fluid the fluid stream wherein a fluid sample of the fluid stream is collected along a line spanning the inner diameter of said pipe, even where there is present entrained liquid particles and even flowing liquid droplets/streams along the lower and/or upper surfaces of the pipe. While the present figures illustrate the position of the probe tip as vertical, this is not intended to be limiting, as the probe can be oriented at any angle relative the pipe, as long as the probe interface (insertion point) allows it.

The slot and outflow passage are preferably relatively narrow (less than 1/32" depending on the volume of fluid being sample, the speed, viscosity, and other factors) to remove a very thin slice of the total breadth of the fluid stream, so as to provide an accurate composite of the total fluid flow using principals similar to the integral principle as used in calculus.

As described, the body 101 has first 103 and second 103' ends defining a length 107 therebetween, with a slot 108 defining a narrow opening to a centrally disposed outflow passage 113 of preferably equal or less diameter than the slot width, thus providing the "integral slice" (in the present example, less than 1/32" wide slot from the outer surface of the probe) to intersect the small ID outflow passage (less than 1/32"), so that process fluid having sample gas containing entrained liquid therein passes into the slot then is urged through the outflow passage to the probe at an equal or higher velocity than the fluid stream, so as to preserve the composition of the fluid stream and prevent disassociation of same.

Continuing with FIGS. 1-9, the threaded end 114 of slotted probe tip 2 threadingly engages the second end 102' of probe P. Probe P has a passage 8 formed therethrough along its length, the probe P having an outer diameter 24 formed allow its length to pass through probe isolation valve 3 (while in an open position) for selective insertion of the probe tip through 8 isolation valve 3, and into the fluid stream in pipe via passage 20.

The probe has formed therethrough along its length a probe passage 8 to provide for the passage of fluid from the probe tip 2 there through. In the preferred embodiment of the present invention, a capillary tube 116 (in the present embodiment, formed of stainless steel) is provided having a length and first 117 and second ends 117' and is situated through the length of probe passage 8, the second end 117' of capillary tube 116 formed to engage the outflow passage 113 of probe tip 2 at a receiver 120 formed within the threaded area 114 of probe tip 2, the first end 117' of capillary tube 116 sealingly engaging the probe tip's outflow passage 113 via first o-ring 121. The second end 102' of insertion probe P engages the probe tip 2 via o-ring 122 at retainer 119', providing sealed connection.

The capillary tube 116 in the present embodiment passes through the length of probe passage 8, the o-ring 121' at first end 117 of capillary tube engaging a flow component 127 (in this case, a 90 degree angle connector), and is sealed via o-rings and positioned to align with a capillary flow passage for flow to the conditioning components downstream, in the present case, the flow would run from capillary tube to regulator inlet 6, where any entrained liquid in the flow is vaporized by a heated regulator or vaporizer.

The capillary tube 116, like the probe tip 2 has an ID formed to facilitate capillary tube capillary flow properties in the fluid flowing therethrough, which, in the present case, for wet gas (natural gas having entrained liquid) has been found to exist in a passage having an inner diameter of less than 1/32", although this figure could vary depending upon the surface tension of the liquids and other factors, further, the geometry of the capillary tube passage facilitate the flow of fluid therethrough at least at the velocity of the fluid stream from which the sample is taken, or at a higher velocity thereto.

In the present exemplary embodiment of the invention, the capillary tube 116 comprises Dursan 1/8" OD stainless steel tubing, which is situated inside the probe passage (and rack), and the present tubing having a 0.030" or less ID to prevent sample disassociation via capillary action (and maintaining or providing enhanced fluid velocity), the optimal diameter of which can vary significantly depending upon the operational criteria and "wet gas" composition.

In the system of the present invention, it is imperative that no disassociation takes place in the sample fluid flow, from the moment the sampling occurs at the slotted probe tip, through the length of probe P (in the preferred embodiment, via capillary tube 116), to regulator inlet 6 (where the sample is conditioned via heated regulator and vaporized).

In the alternative to a capillary tube 116, the inner diameter (ID) of probe passage 8 itself could have an ID formed to maintain or increase flow velocity from the probe tip along its length, and accordingly have an ID equal to or less than the width of the opening forming the slot 108 in the slotted probe tip 2 or ID of the outflow passage 113 (i.e., less than 1/32"), the geometry formed to provide capillary action in the wet gas flowing therethrough to prevent disassociation thereof.

Continuing with FIGS. 8A-8D, the slotted probe tip 2 of the present invention can include on the back side 128 opposite slot opening 106 threaded apertures 129, 129', 129" formed to threadingly receive screws or other fasteners to facilitate the attachment of a cylindrical filter screen 130 (for example, 40×40 mesh, 0.010" wire), to envelope the outer diameter (OD) of the probe tip and prevent solids from entering the opening 106 to slot 108, but large enough for the velocity of the sample to keep fluids from accumulating. A bottom screen disc may also be provided at the second end 103' of slotted probe tip 2 held in place with a spiral retaining ring.

The system of the present invention ensures that the representative sample taken either in spot, batch or continuous fashion is not allowed to disassociate by providing the very small internal cavity forming the outflow passage, to maintain or enhance the fluid flow velocity through the system. The pipeline area is very large compared to the probe's very small interior and because of this vast difference, fluid in the outflow passage from the slotted probe tip to the probe will always be flowing at a higher velocity than the pipeline fluid.

The high gas velocity (higher than the source velocity of the pipeline) of the very small internal cavity/fluid outflow passage is formed to sweep all of the liquid particles at the same velocity as the gas particles being transported from the source to the probe. Therefore, it would remain "associated" with the gas from which it condensed, as verified from Applicant's own empirical testing. High velocity gas in the small internal diameter bore forming outflow passage engaging the relatively narrow slot of the probe will prevent any significant layer of liquid from accumulating on the surfaces. Even if an ultra-thin layer were to coat the probe's interior, the total area is anticipated to be small that the impact would be expected to be negligible.

Continuing with the figures, as shown, the slotted probe tip 2 of the preferred embodiment of the present invention is engaged to the capillary tube (when utilized) then the end of an insertion probe P then is lowered or inserted (e.g., via the rack in the preferred embodiment) into a pipeline positioned in the medial or center-third area 21 of the pipe with the opening 106 forming the entrance of the slot 108 facing the flow stream. While the present illustration shows the sampling position of the probe such that the probe tip 2 is in the center-third area 21 for BLM compliance, it is noted that the probe tip can be positioned elsewhere as required.

A portion of the fluid stream comprising a "linear slice" of the fluid flow in the positioned portion of the pipe then passes into the opening, into and through the slot, then through the pressure of the flow stream is urged through the outflow passage, capillary tube with capillary flow on to the modular conditioning components for heating and/or collection, online analysis, monitoring, or other usage. As earlier indicated outflow passage in the preferred embodiment as well as downstream the probe tip to the conditioning components preferably has an inner diameter commensurate with the width of the slot formed in the body forming the slotted probe tip, resulting lesser area than the slot, so as to facilitate at least equal but more likely greater fluid velocity flow through said outflow passage, to keep the fluid from slowing and possibly disassociating.

Along with the higher velocity sweeping the wet gas sample so that it does not disassociate, conventional science recognizes that, as the inside diameter or cross sectional area of a slot or passage decreases, a static liquid having sufficient surface tension will interact with the walls of sufficiently small slot or passage to trigger static capillary functionality, a phenomenon known to occur when the static liquids adhesion to the walls is stronger than the cohesive forces between the liquid's molecules. Such a phenomenon, in combination with the higher velocity sweep, is believed to be an inherently motivating feature in the present invention when wet natural gas passes through the slot or wall when the clearance is at most (depending on various factor) equal or preferably generally less than 1/32", although the exact threshold where static capillary function can and will occur in this dynamic sweeping combination can vary depending on the composition of the wet gas, as well as other factors.

In the preferred embodiment of the present invention, the sample, once taken, is then directed to a heated conditioning component(s) to vaporize any liquids, providing a single phase sample, then to a process analyzer, monitor, sample container, or other end use.

Considering the above and foregoing, a method of sampling a wet gas from a fluid stream the present invention could therefore comprise the steps of, for example:

a. providing a probe having a probe passage formed along its length having an inner diameter having a geometry to facilitate capillary action in wet gas flowing therethrough, at a higher velocity than said fluid stream;

b. allowing wet gas to flow from said fluid stream into and through said probe so as to provide capillary action at the higher velocity;

c. allowing said capillary action to prevent disassociation of said composition of said wet gas as it flows through said probe passage.

Still further, the method of sampling a wet gas comprising gas with entrained liquid in a fluid stream of the present invention could comprise, for example, comprising the steps of:

a) providing a probe tip 2 engaging probe P, said probe tip comprising an elongated slot situated along its length;

b) laterally positioning said probe tip in the fluid stream so that said slot faces the stream;

c) utilizing said slot to receive a linear sample of flow of said stream into said body, providing received flow;

d) flowing said received flow through a passage sized to have capillary flow properties to prevent disassociation; and e) vaporizing said received flow to provide a representative sample.

As discussed, to be compliant with present BLM regulations, preferably the probe tip 2 would be situated in the center third (medial area) of the flow.

While less than 1/32" is indicated as an example of the diameter for capillary flow in the present wet gas application, it is reiterated that the optimal specific geometry can vary depending on a number of criteria. A combination of phase diagram data and empirical testing could be used as a guide to determine the optimum capillary diameter/geometry for the particular wet gas composition, taking further into account the particular pipeline/flow property/application/environmental and other factors.

Heat Trace Interface for Modular Conditioning Components

FIGS. 11A-25 teach first and second embodiment of a heat trace interface wherein there is provided first and second thermal conductor plates formed to envelope and engage a heat trace or the like, said thermal conductor plate channels specifically formed to facilitate heat transfer from the heat trace to modular conditioning components, evenly distributing the heat, as will be further discussed, infra.

Heat Trace Interface for Heated Regulator

Figure 11:
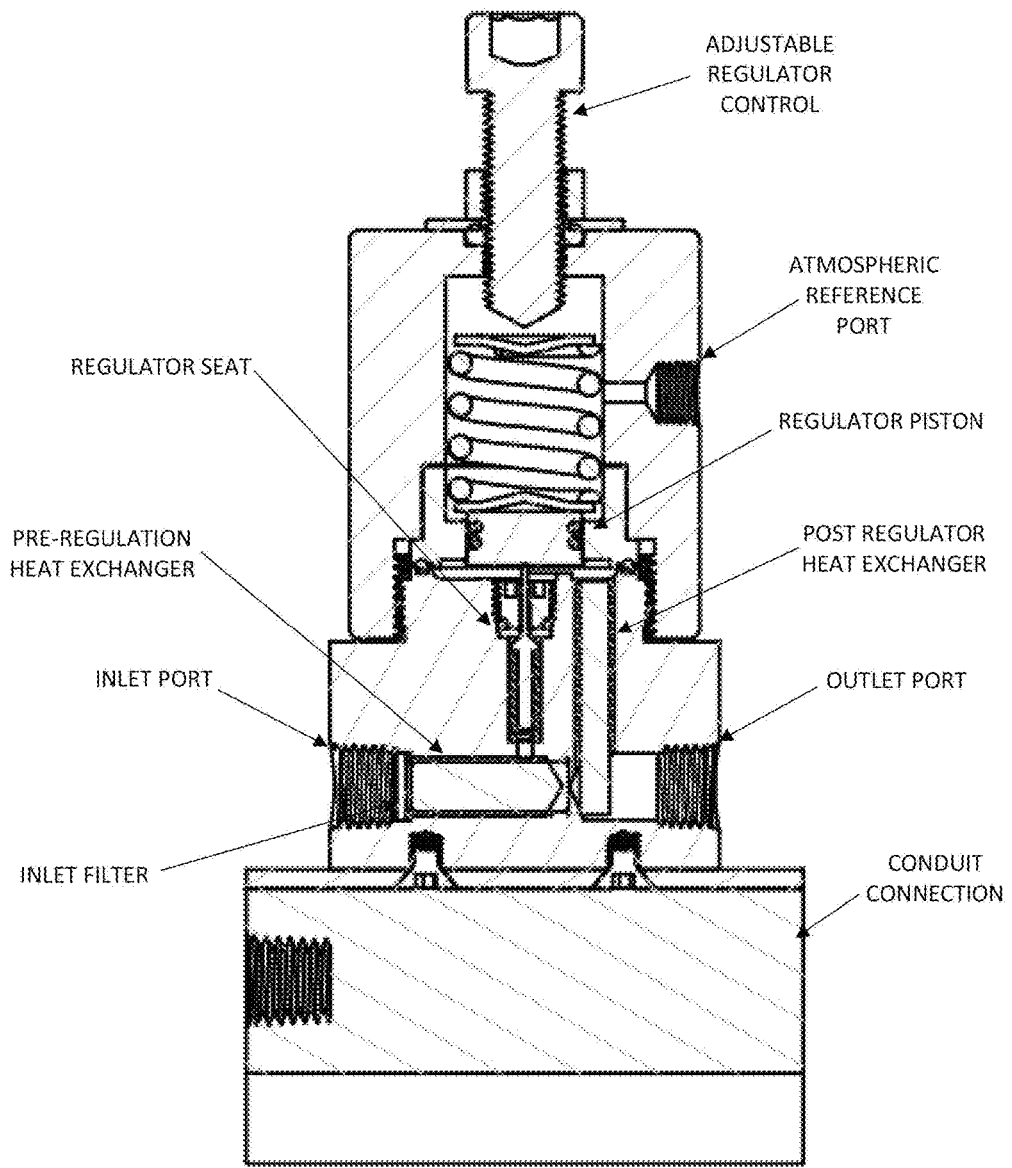
FIG. 11 is a side, partially cutaway view of the A+ GENIE brand heated regulator first commercialized in 2004 and as such comprises Applicant prior art, with pre and post-heat exchange features, and which requires an external source of electrical power.
Figure 11A:
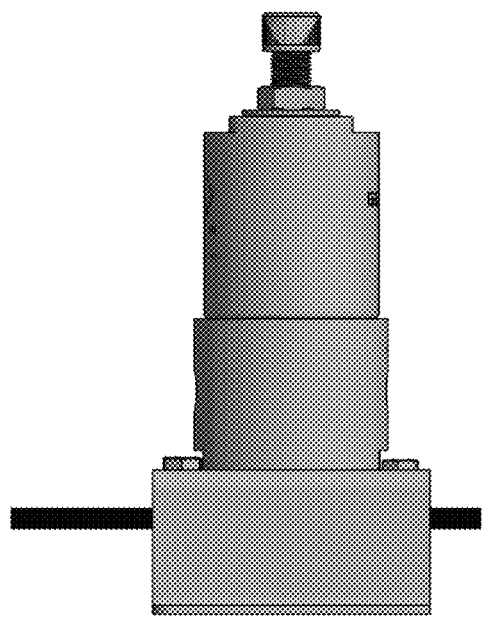
FIG. 11B is an end view of the device of FIG. 11A.
FIG. 11C is a side view of the device of FIG. 11A, in line drawing form.
FIG. 11D is an end view of the Device of FIG. 11B, in line drawing form.
Figure 11B:
Figure 11C:
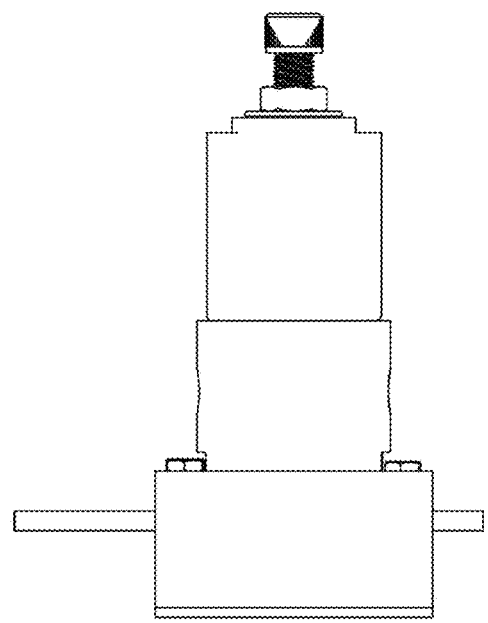
Figure 11D:
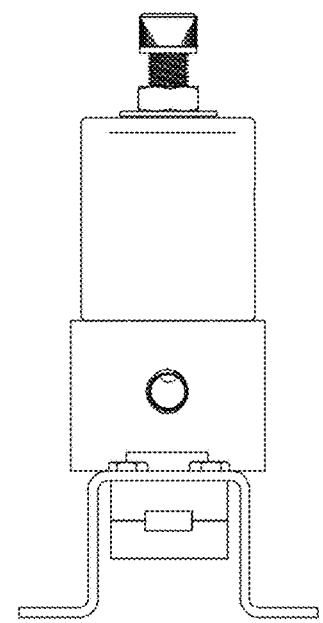

The first embodiment of the heat trace interface is configured to provide heat to a heated regulator. FIG. 11 shows the applicant's Genie Heated Regulator (GHR) with pre-regulation heat exchange and post regulator heat exchange commercialized in 2004, a design that requires electrical power.

FIGS. 11A-11D show the new, improved regulator configuration of the present invention which utilizes a similar regulator functions as the earlier system, but with the added improvement of a new interface incorporating enhanced heat transfer to dispense with the need for electrical heating, the system utilizing including heat pipes emanating from a base formed to receive thermal energy, the heat pipes engaging thermal conductor plates that evenly distribute the heat and formed to interface with a conventional heat trace, the heat plates conducting thermal energy to the heat pipes, which in turn heat valve stem pressure drop area of the regulator in the base of the regulator to heat the regulator without the need for separate electrical power lines, as in prior art devices, as will be described below.

Figures 12A, 12B:
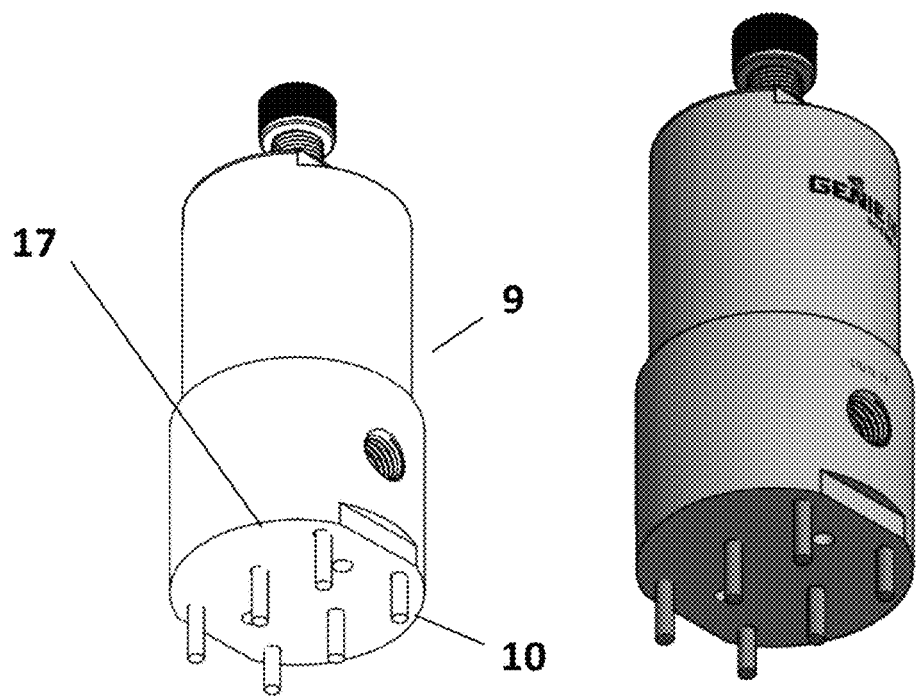
FIG. 12A is an isometric view of the device of FIGS. 11A-11D, illustrating the regulator 9 having heat pipes 10 emanating therefrom.
FIG. 12B is a view of the device of 12A in greyscale.
Figure 13:
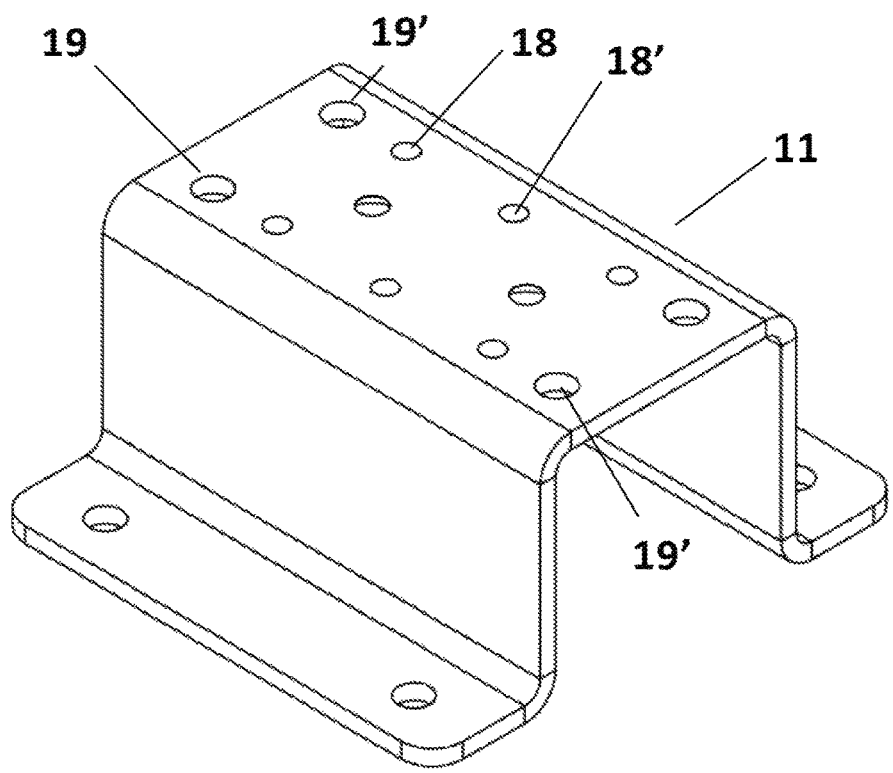
FIG. 13 is a close-up view of the device of mounting bracket 11 of FIGS. 11A-11D, having holes for receiving the heat pipes 10 of FIG. 12A therethrough.

FIG. 12 shows six heat pipes 10 pressed into the base 17 of the regulator 9 to facilitate heat transfer to the base that contains the valve stem where the pressure drop takes place. FIG. 13 is an isometric view of the bracket 11 used with the regulator, the bracket having formed therein passages 18, 18' for allowing the heat pipes to pass therethrough, as well as apertures for the passage of a threaded fastener from the regulator.

Figure 14:
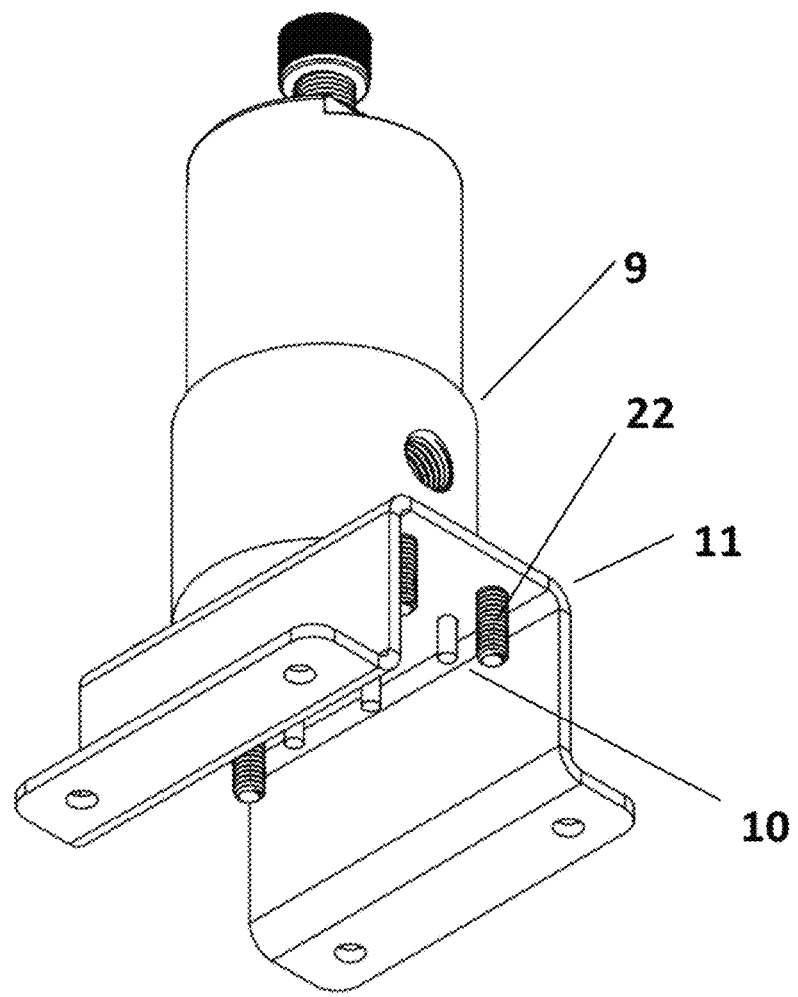
FIG. 14 is a perspective view of the invention of FIG. 12A, illustrating the mounting of the regulator to the support bracket and heat pipes 10 emanating therefrom.

FIG. 14 shows the bracket 11 attached to the regulator 9 with heat pipes 10 and threaded fasteners 22 passing therethrough.

Figures 15A, 15B:
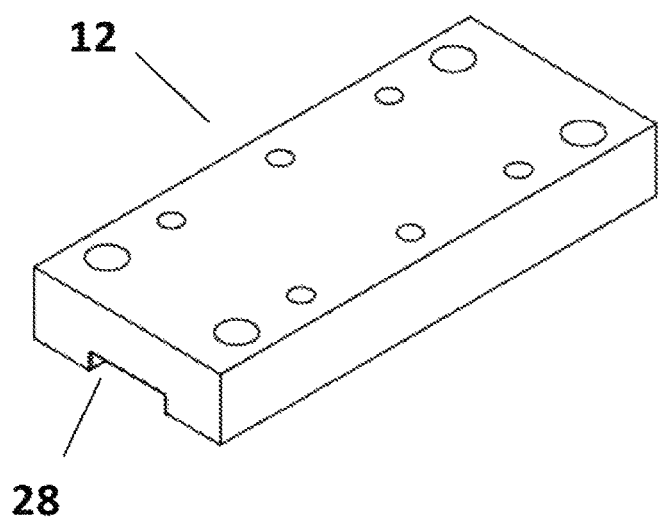
FIG. 15A is an upper, perspective view of metal conductor (Aluminum shown) first and second substrate halves or thermal conductor plates 12, 13, respectively, bolted around a heat trace to engage the heat pipes 10 of FIG. 14.
FIG. 15B is a lower, perspective view of the substrate halves or thermal conductor plates of FIG. 15A, having a channel formed along its lower surface along its length for engaging a heat trace for thermal conduction to heat pipes 10 engaged thereto.

FIGS. 15A and 15B show first and second thermal conductor plates 12, 13, respectively, that have formed along their lengths longitudinal channels 28, 28' respectively, which plates are configured to join such that their respective channels engage an existing heat trace, the channels being formed to receive the heat trace therebetween, with the thermal conductor plates bolted around the existing heat trace so that the conductor plate channels envelope same, engaging the heat trace to facilitate evenly distributed thermal heat transfer therefrom.

Figures 16A, 16B:
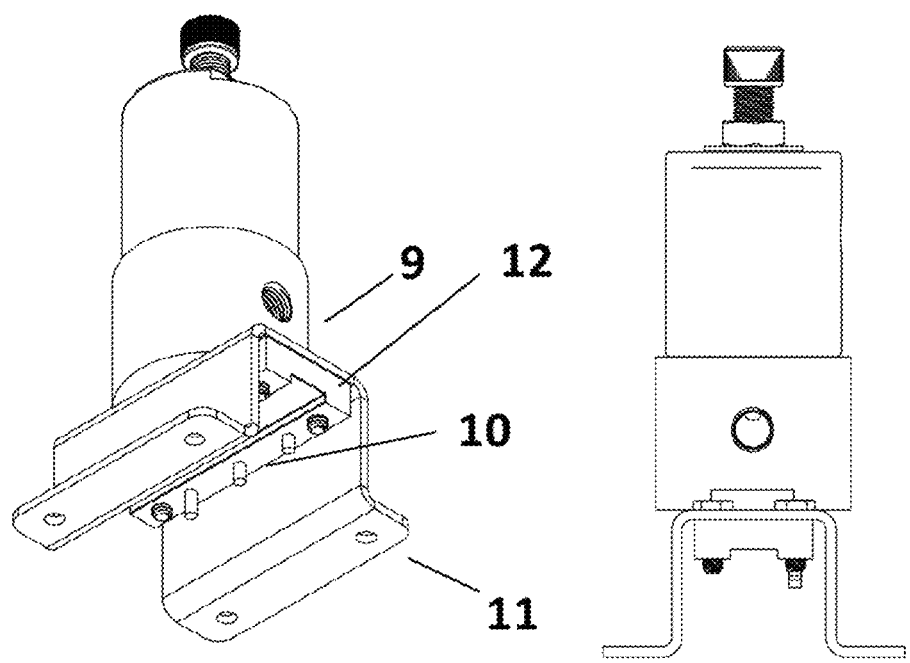
FIG. 16A is a perspective view of the device of FIG. 14 illustrating the metal conductor plate 12 engaging the heat pipes 10 of the regulator 9.
FIG. 16B is an end view of the invention of FIG. 16A.

FIGS. 16A and 16B show the first thermal conductor plate 12 added to the bracket 11 with the regulator 9 mounted thereon so that the heat pipes 10 from the regulator base engage first thermal conductor plate 12.

Figure 17:
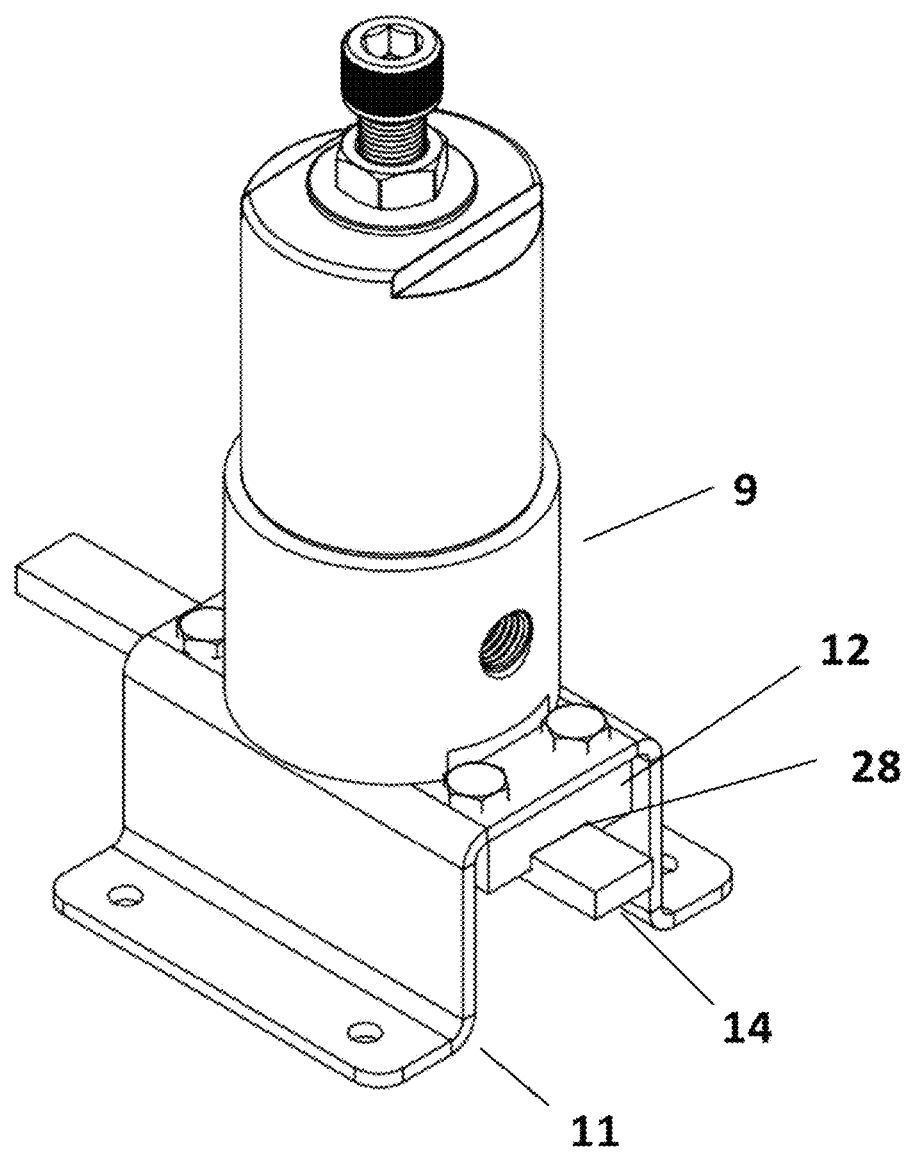
FIG. 17 is a perspective view of the invention of FIG. 16A, with the addition of a heat trace engaging the lower surface of the first metal conductor plate 12 halve via the channel formed along its lower surface shown in FIG. 15B.

FIG. 17 adds the heat trace 14 to FIG. 16, engaging the thermal conductor plate 12 via channel 28.

Figure 18:
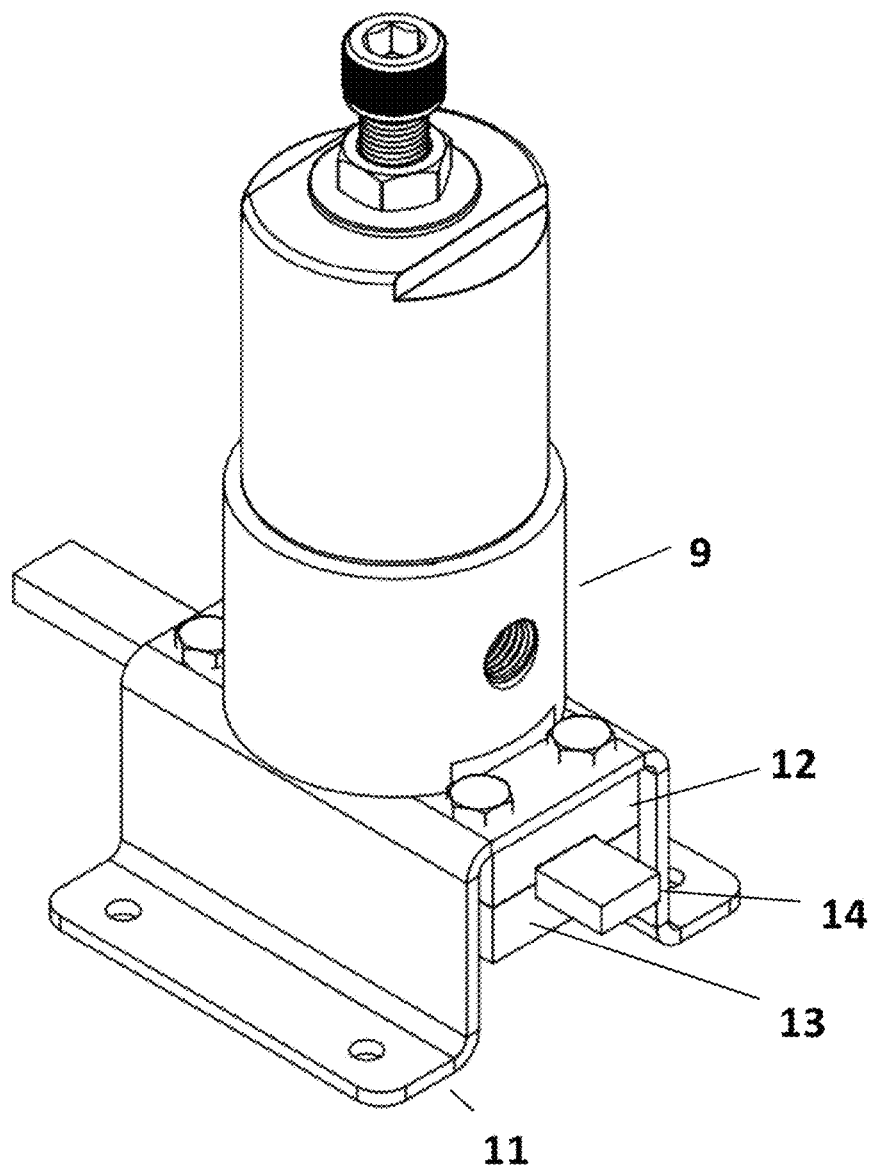
FIG. 18 is a perspective view of the invention of FIG. 17, with the addition of the second metal conductor plate 13 having an upper channel along its length engaging the heat trace, the first 12 and second 13 metal thermal conductor plates engaged to the bracket 11 via threaded fastener.

FIG. 18 adds the second thermal conductor plate 13 to engage first thermal conductor plate 12 so as to envelope the heat trace 14.

Figures 19A, 19B:
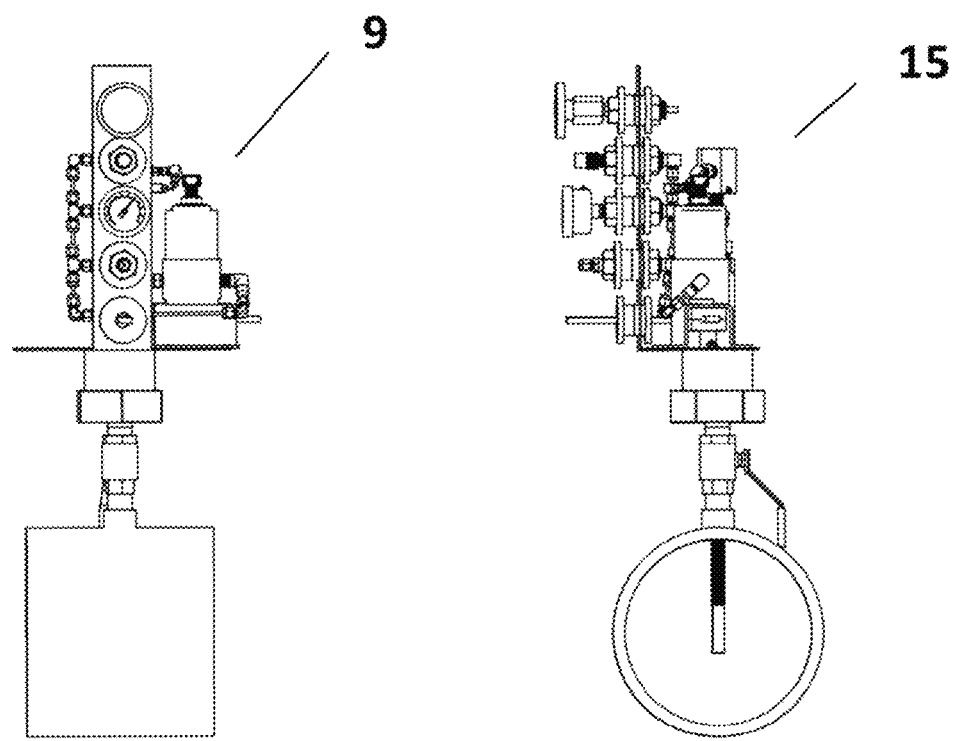
FIG. 19A is a frontal view illustrating the regulator with heat pipes engaging the heat trace of FIG. 18 mounted to a bracket, forming a heated component in a modular sample conditioning system comprising modular sample/conditioning components, at the pipeline.
FIG. 19B is an end view of the invention of FIG. 19A, illustrating a sample probe situated in the pipeline, the pipeline containing a fluid stream, the sample probe tip positioned to facilitate the collection of a linear sample of fluid from the center-third area of the fluid stream, and direct same to the heated modular conditioning components.

FIGS. 19A-19C shows the regulator 9 with thermal conductor plates 12, 13 engaging the heat trace, the regulator mounted on bracket 15 forming a component of modular sample conditioning system 5.

In use, the heat trace is powered via solar panel or the like, which heats the heat trace along its length. The heat of the heat trace is conducted via the thermal conductor plates, through the heat pipes, to provide evenly distributed heat via the base of the regulator.

Heat Trace Interface for Vaporizer

A second embodiment of the heat trace interface is configured to provide thermal energy to a Vaporizer or the like.

The A+ brand Vaporizer (GV) with single path vaporization including thermal isolation and a brass thermal conductive insert was first commercialized in 2004 (FIG. 20), providing vaporization when the liquid load would overwhelm the above discussed Genie Heated Regulator (GHR) alone. The device shown in FIG. 20 utilized electricity from an external source to power a high wattage electric heater, thus requiring electrical power to the vaporizer for operation.

Figure 20:
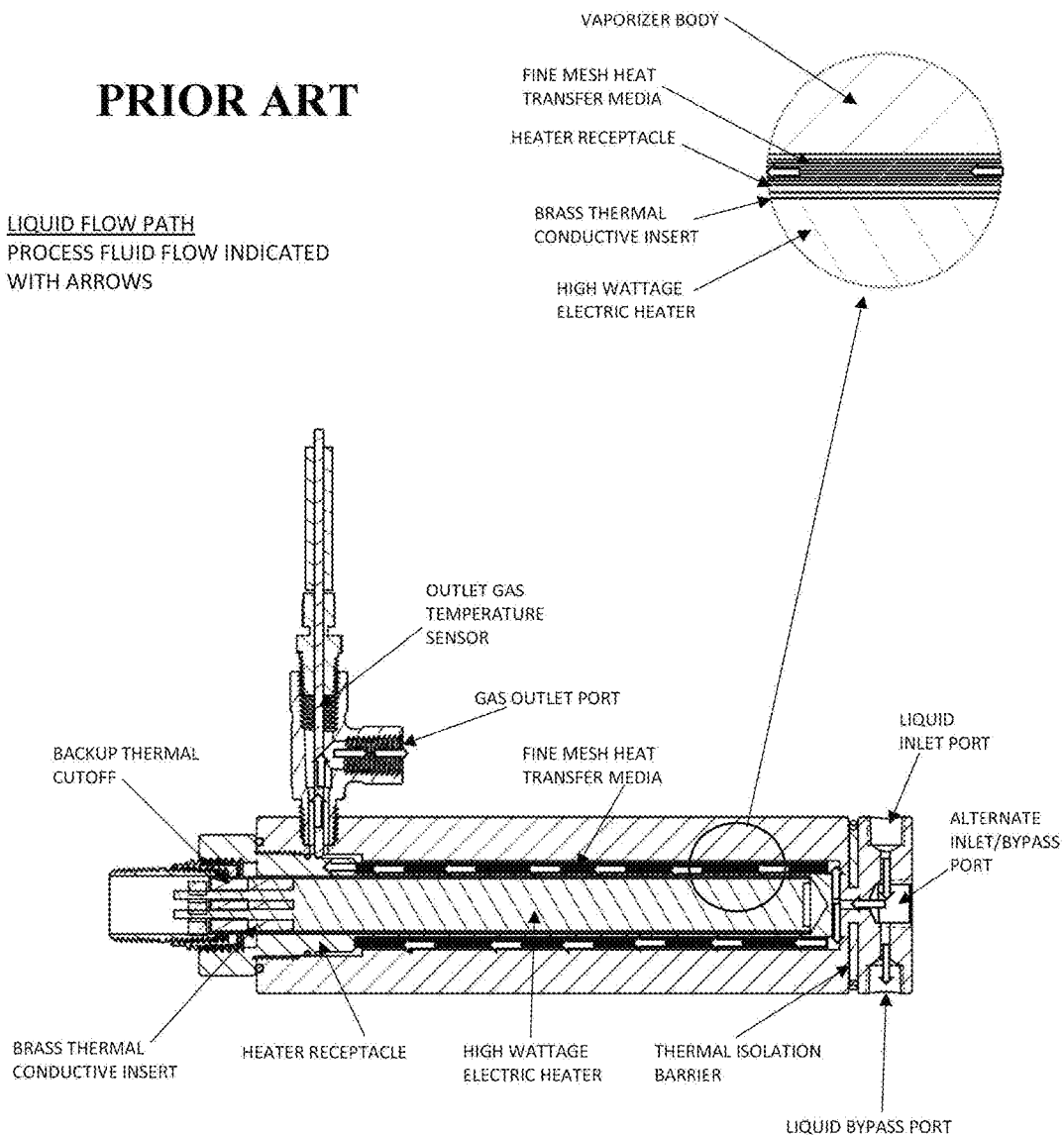
FIG. 20 is a side, partially cross-sectional, partially cutaway view of an exemplary A+ GENIE brand vaporizer utilizing an electric heater (Applicant prior art) which may be modified for use in a alternative embodiment of the present invention.
Figures 23A, 23B, 23C:
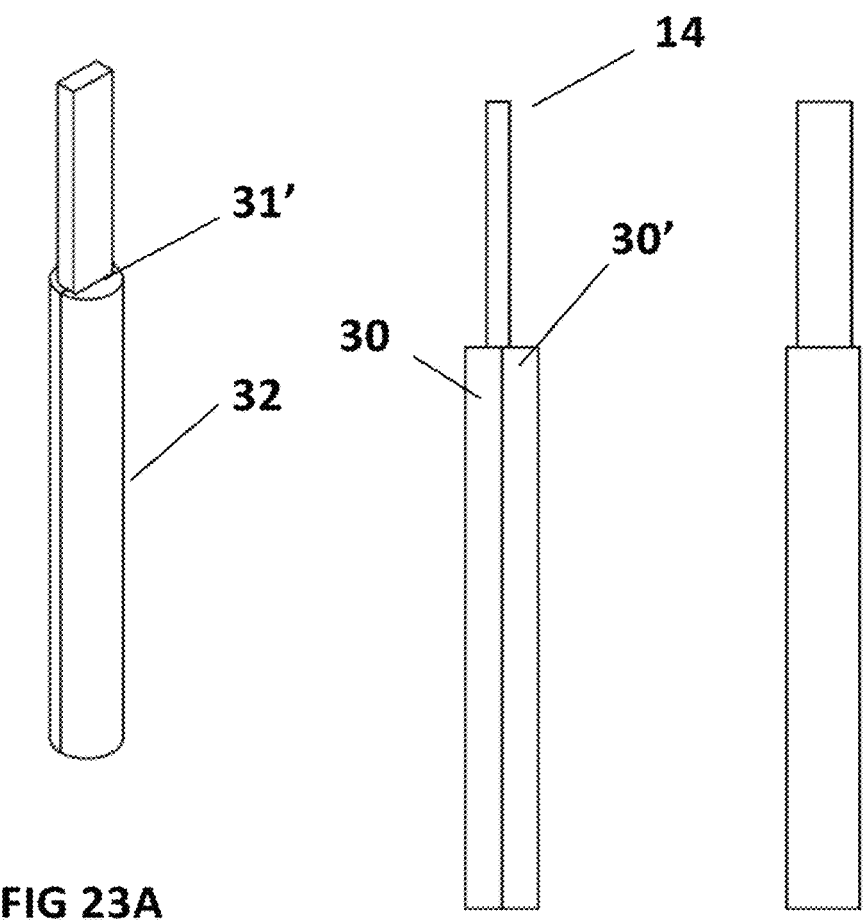
FIG. 23A is a perspective, close-up view of the embodiment of the invention of FIG. 22A, but with the second heat conducting cover engaging the heat trace, with the first heat conducting cover enveloping same (heat conducting cover a/k/a brass cover halves or sleeves).
FIG. 23B is an edge view of the invention of FIG. 23A, illustrating the thermal conducting plates 30, 30" having slots formed along their lengths to engage opposing sides of heat trace 14, enveloping same.
FIG. 23C is a side view of the invention of FIG. 23A.

The improvement of the present system over the prior art of FIG. 20 is shown in FIG. 21A-25B, providing a vaporizer requiring no electrical power for the vaporizer to function.

The electric heater cartridge and controller (thermal cut-off) insert shown in the old design of FIG. 20 is removed from the heater cartridge housing and replaced by a thermal core in the form of first 30 and second 30' thermal conductor plates having channels 31, 31' along their length formed to envelope a heat trace 14 at the site, and (at least in the present exemplary embodiment) fit within the heater housing for insertion into the vaporizer. All of the benefits and features of the existing vaporizer would still apply, but without the necessity of electrical power or control. The new vaporizer design is detailed in FIGS. 22-25B. FIGS. 22A-22C show the existing heat trace 14 with one of two thermal conductor plates, the first 30 thermal conductor plate. As shown in FIGS. 22A-23C, the first 30 and second 30' thermal conductor plates are formed 31, 31' along their length, respectively, to engage, envelope, and contact the heat trace 14 to facilitate thermal transfer from same, the engaged plates formed to provide an outer radial surface 32 having an outer diameter 32' (FIG. 24C). The thermal conductor plates are preferably formed from a material with a high degree of thermal conductivity, such as brass, to provide even heat distribution.

FIGS. 24a-24c shows the thermal conductor plates 30, 30' engaging a heat trace 14 situated with the vaporizer heater cartridge housing 33, which itself is formed of thermally conductive material. This housing is of the type which previously was formed to contain the electrically heated cartridge and brass sleeve of the earlier device of FIG. 20. The heater cartridge housing 33 is shown as cylindrical and has a receiver formed therein having an inner diameter 34 formed to slidingly receive, envelope and engage the outer diameter '32' of the engaged thermal conductor plates 30, 30' enveloping heat trace 14.

However, in the present device, the housing has no electrically heated cartridge and instead contains the heat trace 14 and thermal conductor plates 30, 30'.

Figure 25A:
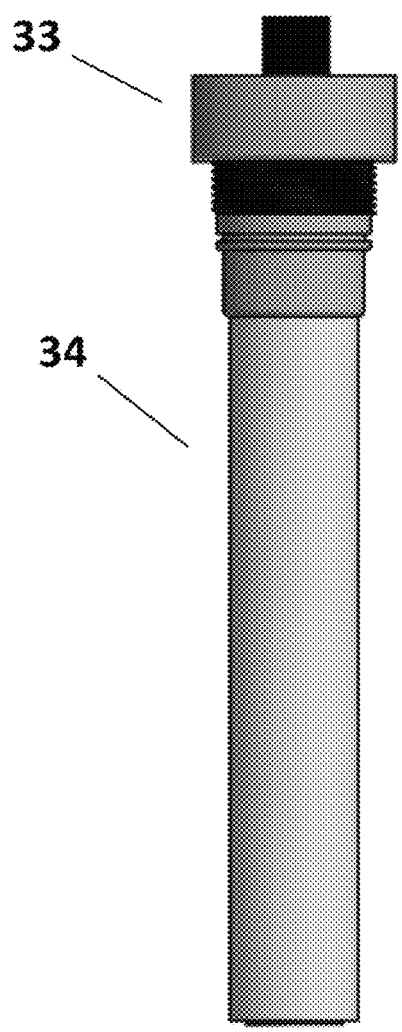
FIG. 25A is a side view of the invention of FIG. 24A providing a full view of the heat trace engaging cartridge comprising housing 33 and mesh screen.
Figure 25B:
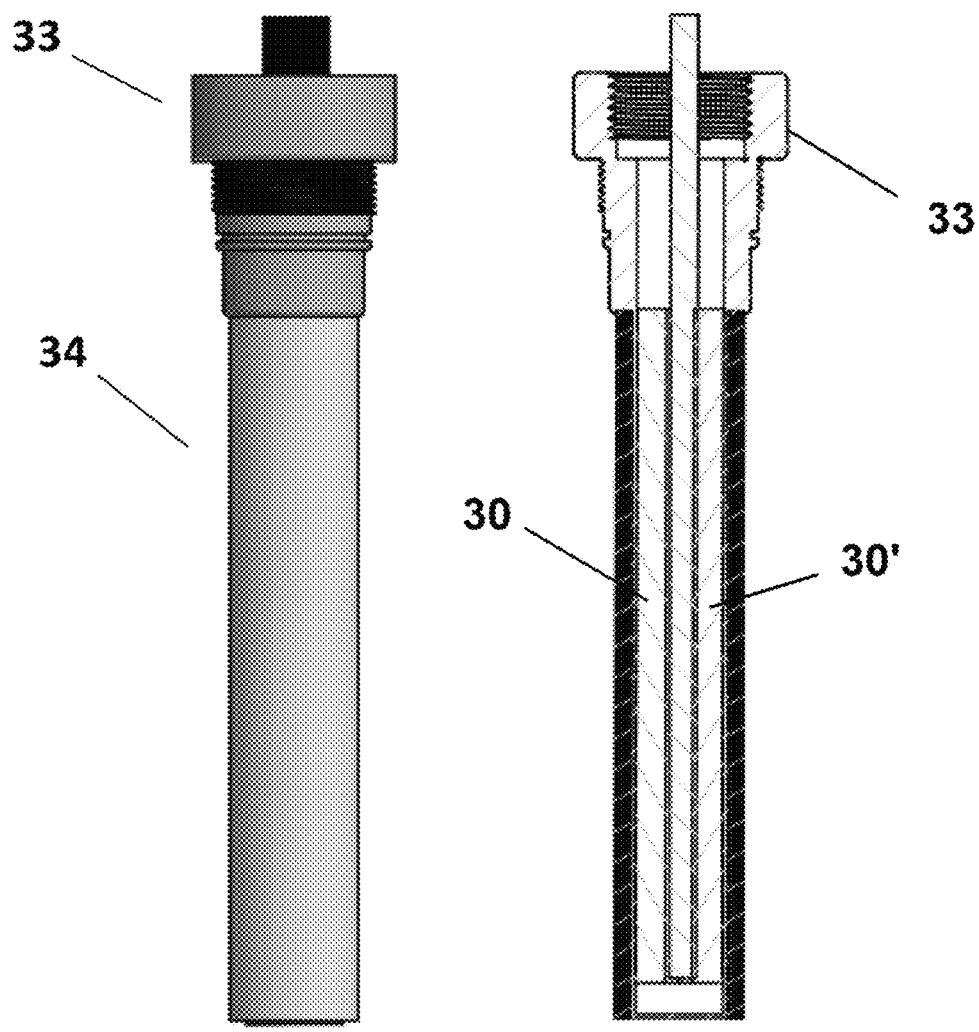
FIG. 25B is a side, cross-sectional view of the invention of FIG. 25A, illustrating the heat trace, first and second heat conducting covers 30, 30', housing 33 and screen for heat transfer, formed to replace heater receptacle for the vaporizer of FIG. 20.

FIGS. 25A and 25B shows the heater cartridge housing 33 with fine mesh screen 35 wrapped around it (see FIG. 20). FIGS. 25A-25B shows the assembled vaporizer of the present invention that does not need electrical power.

A third embodiment entails retrofitting existing GHRs (FIG. 10) and GVs (FIG. 20) in existing applications and locations to remove the need for electrical power if they are now used in BLM regulated areas with limited power that must comply with Order No 5. See FIGS. 11 and 21.

A fourth embodiment adds the A+ GENIE brand Membrane Separator with Liquid Block (U.S. Pat. No. 7,555,964) just before the analyzer.

ELEMENTS OF THE INVENTION

P insertion probe
1 gas with entrained liquids
2 slotted probe tip
3 probe isolation valve
4 substrate coupling
5 modular sample conditioning system
6 regulator inlet
9 regulator 10 heat pipes
11 bracket
12 thermal conductor plate (AL)
13 thermal conductor plate (AL)
14 heat trace
15 bracket—modular sample conditioning system
16 enclosure
17 regulator base
18,' heat sink passages
19, 19' bolt passages
20 probe passage
21 medial area of pipe/stream
22 regulator threaded fasteners
24 OD of probe
25, length, rack'
28, 28' conductor plate channels
30, 30' thermal conductor plates
31, 31' channels for receiving heat trace
32,' outer surface, OD
33 heater cartridge housing
34 Inner diameter of heater cartridge
35 mesh screen
101 body
102,' insertion probe first, second ends
103,' first, second ends of body 101
104 outer wall
105 longitudinal axis
106 opening
107,' length, width
108 slot
109 O-Ring saddle (probe tip)
110 opening 106 ends
111,' first, second side walls
112,' outer, inner edges
113 outflow passage
114 threaded end of probe
115 ID outflow passage
116 capillary tube
117,' first, second ends
119 O-Ring retainer
120 receiver
121,' O-Ring,"
122 Probe lower end O-ring seal
127 flow component
128 back side of probe opposite slot opening
129,',' threaded apertures
130 solids filter screen The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

I claim:

1. A device for sampling a wet gas having a composition in a fluid stream, comprising:
   a probe having a probe passage along its length having an inner diameter;
   a probe tip affixed to said probe having a slot formed therein leading to an outlet passage;
   said probe passage formed to facilitate capillary action in wet gas flowing therethrough;
   whereby, wet gas flows from said fluid stream, through said slotted probe tip, then into and through said probe passage so as to facilitate capillary action and flow therethrough and prevent disassociation of said composition of said wet gas.

2. The device of claim 1, wherein said slot of said probe tip forms an opening having a width of less than $1/32$", and said outlet passage of said probe tip has an inner diameter less than $1/32$", said slot and outlet passage of said probe tip formed to facilitate capillary action in wet gas flowing therethrough.

3. The device of claim 1, wherein said probe tip is formed to receive a sample flow from the center third of said fluid stream.

4. The device of claim 1, wherein said fluid stream flows through a pipe having a inner diameter, and said probe tip further comprises:
   a body having first and second ends and a length,
   said body having said slot having a width and a length situated along the length of said body, said slot having a width of less than $1/32$", said slot engaging said fluid stream so as to facilitate the flow of fluids therethrough at least at the flow velocity of said fluid stream;
   whereby, after laterally positioning said probe tip into said pipe and positioning said slot to face the flow of said fluid stream to collect the center third of said fluid flow, said slot receives a portion of wet gas from said fluid stream through said slot without reduction in flow velocity while preventing disassociation of the entrained liquid from the gas, providing a representative sample of said fluid stream.

5. The device of claim 4, wherein said outlet passage and said probe passage are formed to receive said representative sample therethrough via said slot, respectively, and wherein said outlet passage and said probe passages facilitate capillary action in said representative sample flowing therethrough, so as to prevent disassociation thereof.

6. The device of claim 5, wherein said inner diameter of said outlet passage and said probe passage facilitate capillary action in said wet gas flowing therethrough.

7. The device of claim 6, wherein said outlet passage and said probe passage have an inner diameter of less than $1/32$".

8. The device of claim 7, wherein said probe comprises an insertion probe with said probe tip mounted thereto.

9. The device of claim 8, wherein said length of said slot corresponds to a targeted collection area associated with said fluid stream flowing through said pipe.

10. The device of claim 9, wherein said slot is formed to facilitate collection of a sample of said fluid stream flowing through a middle third of said inner diameter of said pipe.

* * * * *